United States Patent
Richard et al.

(10) Patent No.: US 9,315,834 B2
(45) Date of Patent: Apr. 19, 2016

(54) MANUFACTURE OF XYLONIC ACID

(75) Inventors: Peter Richard, Espoo (FI); Marilyn Wiebe, Espoo (FI); Mervi Toivari, Espoo (FI); Dominik Mojzita, Espoo (FI); Laura Ruohonen, Espoo (FI); Merja Penttilä, Espoo (FI)

(73) Assignee: Teknologian Tutkimuskeskus VTT, Espoo (FI)

( * ) Notice: Subject to any disclaimer, the term of this patent is extended or adjusted under 35 U.S.C. 154(b) by 662 days.

(21) Appl. No.: 13/256,559

(22) PCT Filed: Mar. 17, 2010

(86) PCT No.: PCT/FI2010/050205
§ 371 (c)(1),
(2), (4) Date: Sep. 14, 2011

(87) PCT Pub. No.: WO2010/106230
PCT Pub. Date: Sep. 23, 2010

(65) Prior Publication Data
US 2012/0005788 A1    Jan. 5, 2012

(30) Foreign Application Priority Data
Mar. 18, 2009    (FI) ..................... 20095278

(51) Int. Cl.
C12P 7/58    (2006.01)
C12N 9/06    (2006.01)
C08B 31/00    (2006.01)
C12N 9/04    (2006.01)

(52) U.S. Cl.
CPC ................. *C12P 7/58* (2013.01); *C12N 9/0006* (2013.01)

(58) Field of Classification Search
None
See application file for complete search history.

(56) References Cited

U.S. PATENT DOCUMENTS

| 2003/0166179 A1 | 9/2003 | Rajgarhia et al. |
| 2006/0110810 A1 * | 5/2006 | Rajgarhia et al. ............. 435/139 |

FOREIGN PATENT DOCUMENTS

| JP | 2007-28917 A | 2/2007 |
| WO | 90/03167 A1 | 4/1990 |
| WO | 03/078347 A2 | 9/2003 |
| WO | 2005/068642 A2 | 7/2005 |
| WO | 2006/032530 A1 | 3/2006 |
| WO | 2006/033333 A1 | 3/2006 |
| WO | 2008/091288 A2 | 7/2008 |

OTHER PUBLICATIONS

Chun et al., The Development of Cement and Concrete Additive Based on Xylonic Acid Derived via Bioconversion of Xylose; Applied Biochemistry and Biotechnology; vol. 129-132, pp. 645-658, 2006.*
Rensburg et al., Engineering Yeast for Efficient Cellulose Degradation; Yeast, vol. 14, pp. 67-76, 1998.*
Ahmed, Y.M., "Formation of Xylonic Acid, Xylitol and Xylulose by Cell—Free Extract of Schizosaccharomyces Japonicus", Bull. N R C, Egypt., vol. 22, No. 1, Chapter 6, pp. 51-61, (1997).
Berghäll, S., et al., "Identification in the mould Hypocrea jecorina of a gene encoding an NADP+: D-xylose dehydrogenase", FEMS Microbiology Letters, vol. 277, pp. 249-253, (2007).
Buchert, J., et al., "Production of Xylonic Acid by Pseudomonas fragi", Biotechnology Letters, vol. 8, No. 8, pp. 541-546, (1986).
Hasper, A.A., et al., "The Aspergillus niger transcriptional activator XlnR, which is involved in the degradation of the polysaccharides xylan and cellulose, also regulates D-xylose reductase gene expression", Molecular Microbiology, vol. 36, No. 1, pp. 193-200, (2000).
Kanauchi, M., et al., "Use of Xylose Dehydrogenase from Trichoderma viride in an Enzymic Method for the Measurement of Pentosan in Barley", J. Inst. Brew., vol. 109, No. 3, pp. 203-207, (2003). Abstract Only.
Suzuki, T., et al., "Oxidation and Reduction of D-Xylose by Cell-Free Extract of Pichia quercuum", Appl Environ Microbiol., vol. 25, No. 5, pp. 850-852, (1973). Abstract Only.
Träff, K.L., et al., "Deletion of the GRE3 Aldose Reductase Gene and Its Influence on Xylose Metabolism in Recombinant Strains of Saccharomyces cerevisiae Expressing the xylA and XKS1 Genes", Applied and Environmental Microbiology, vol. 67, No. 12, pp. 5668-5674, (2001).
Zepeda, S., et al., "NADP+-dependent D-xylose dehydrogenase from pig liver: Purification and properties", Biochem. J., vol. 266, pp. 637-644, (1990).
Search Report issued for Finnish Patent Application No. 20095278; dated Sep. 24, 2009; two pages total.
Supplementary European Search Report dated Dec. 8, 2014 for Application No. EP 10753171.7-1501.
Tolvari, M. H., et al., "*Saccharomyces cerevisiae* engineered to produce D-xylonate", Appl. Microbiol Biotechnol (2010) 88, pp. 751-760.
Pezzotti, F., et al., "Enzymatic synthesis of aldonic acids", Carbohydrate Research 341 (2006), pp. 2290-2292.

* cited by examiner

*Primary Examiner* — Addison D Ault
(74) *Attorney, Agent, or Firm* — Ladas & Parry LLP

(57) ABSTRACT

Provided is a method for producing xylonic acid from xylose with a recombinant fungal strain that is genetically modified to express a xylose dehydrogenase gene, which is able to convert xylose to xylonolactone, which is spontaneously or enzymatically hydrolyzed to xylonic acid. The xylonic acid is excreted outside the host cell. Xylonate production may be coupled with xylitol production. Alternatively, if xylitol production is not desired, its production is reduced by removing the aldose reductase (or specific xylose reductase) enzyme, which converts xylose to xylitol. Expression of a heterologous lactonase encoding gene may result in higher acid concentrations. The method is suitable for producing xylonic acid from a hemicellulose hydrolysate such as hydrolyzed lignocellulosic plant biomass.

14 Claims, 8 Drawing Sheets

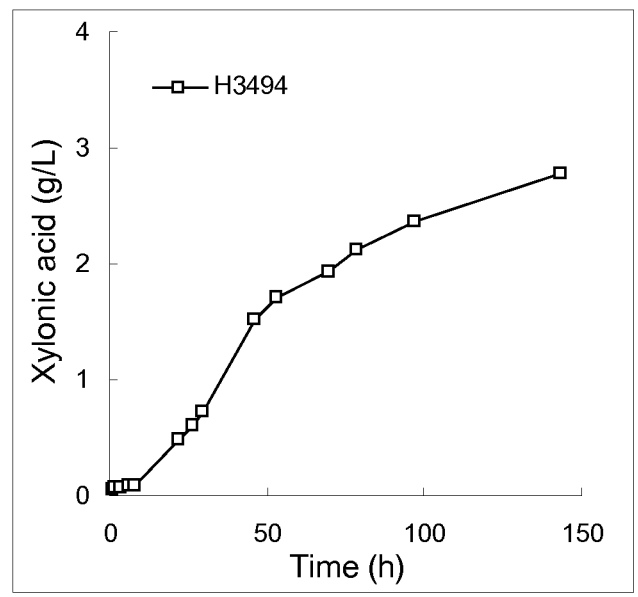
Fig. 10 pH 5.5
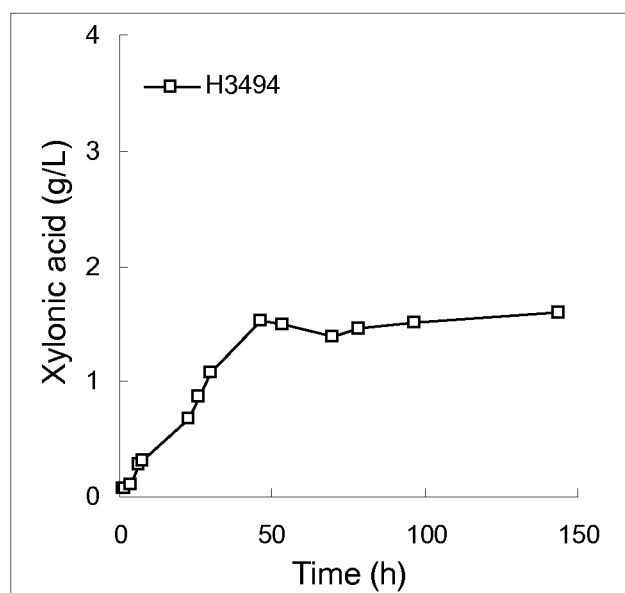
Fig. 11 pH 3.5 a)
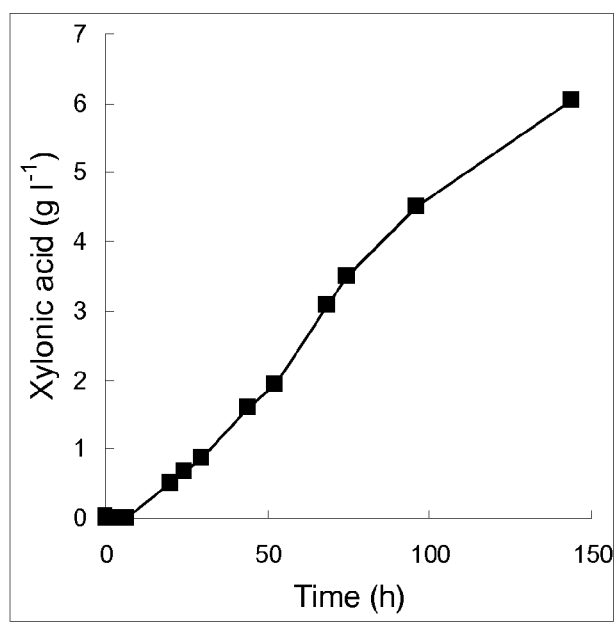
b)
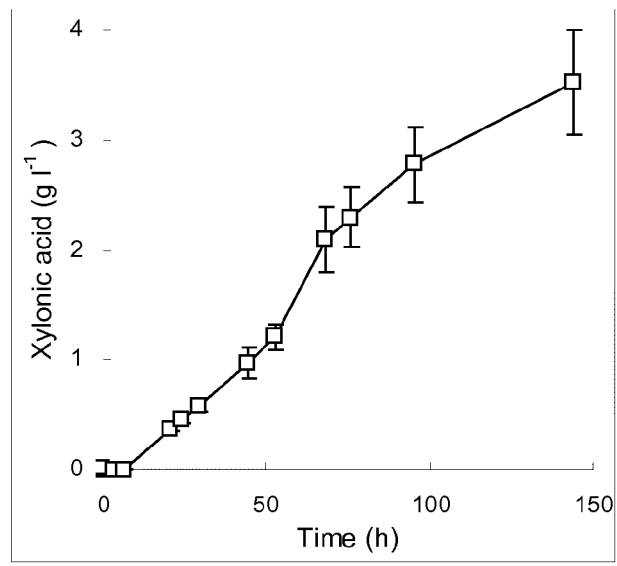
Fig. 12 a) *S. cerevisiae* PR77, b) H3611; pH 5.5, ethanol added at 53 h.

SEQUENCE LISTING

```
<160> NUMBER OF SEQ ID NOS: 40

<210> SEQ ID NO 1
<211> LENGTH: 1176
<212> TYPE: DNA
<213> ORGANISM: Trichoderma reesei

<400> SEQUENCE: 1
atggcgtctg gaaacccttta caccctgaaa tgggcatca tggccaccgg cggaatcgca       60
gagaccttct gcaaggatct cctgtgcaac cccgcgattc gaggcgccga tgatgtgcgc      120
cacgagattg tggccgtggc ctcttccagc agcagcaaga gagcagagga gttcctccag      180
agaatcgacg gtgcctttga cgccaagacg tacggatcat acccggaact tgtggcagac      240
```

```
cccaacgtcg acatcgtcta tgtggcaact ccccacagcc accacttcca gaacaccatg      300
ctggcgctgg aagccggcaa gaacgtcttg tgcgaaaagg ctttcaccgt gacggccgcg      360
caggcccgaa agctggttga cacggccaag gccaagaagc tcttcctgat ggaagctgtg      420
tggacacggt actttccgct gagtatcaag attcgagagc tcattgccgc cggcgagatt      480
ggcactgtct ttcgaacaat cgccgacttg tccatcaacg caaactcaga gcagggtcaa      540
gccctgaaat tcgcagactc acatcgaatg gtcaacccgg acctcgcagg cggtgccacc      600
ttggatctcg gagtctatcc cttgacctgg gtgttccaga ccctgtatca tttgcaaccg      660
gaggaagaca aggaggctcc caccgtggtt gcttccagca caagtacaca cactggcgca      720
gacgagaata ccgccatcat ctgcagcttc cctcgccaca acagcattgg aattgcttcg      780
acgacgatga gggcggacac cgaccccgag aaggacacca ttccggcggt ccgaattcaa      840
ggatccaagg gagaaatcca agtcttcttc ccgacctacc gaccgctcaa gtacaaggtg      900
gtgaagacga acggcgaggc gcagacggtt gactgcccca tccccggaga ccccgcgcgc      960
aagggctcgg gccacggaat gttctgggag gcggacgagt gtgctcgatg ccttcgcgat     1020
ggcaagttgg agagtgccac gttgccatgg aaggagagca ttgtcattat ggaaacgatg     1080
gaggaggcgc tgaggcaggg tggcgtcacg tatccggagc tgattaccac ggatgtctat     1140
gatcccaaga gccctctcaa cacggggaat cagtag                               1176

<210> SEQ ID NO 2
<211> LENGTH: 1083
<212> TYPE: DNA
<213> ORGANISM: Haloarcula marismortui

<400> SEQUENCE: 2
atgaacgttg acgcgctcac gggaggattc gaccgccgag actggcagga acagacagcg       60
accgacaacc cagttcggtt tgcgatgatc ggcgtcggct ggtggaccac cgaacaggcg      120
atgcccgccg tcgacgcagg ggacctctgt gaaacgactg tgctggtcag cagcgaccgg      180
gagaaagcgg cggacgtggc agctgattcg gagacagtcg aacacgcgat tacgtacgag      240
gagttccacg acgcgccgc aagcgacgcg tacgacgccg tctacatcgt caccccgaac       300
gcgctccacc tcccgtacgt cgagacggcg gcagaactgg acaaggcgat cctctgtgag      360
aagccgatgg aggccactat cgagcgcgcc gagcgaatgg tcgaggtctg tgacgagcac      420
gacgcgacgc tgatgatcgc ctaccgaatg cacaccgagc cagccgtccg gcgagcgaag      480
gacctcatcg acgagggta catcggcgaa ccgctgttcg tccacggcaa catgaccgaa       540
cccattcttg aactcgttcc cgaccctgac cagtggcggc tggacgggga actgtccgga      600
gggtgtgccg tcatggatat cggtatctat ccgctgaaca cgagccgatt cctgcttgat      660
gccgaccccg ttgcagtccg ggggaccgtt gcctctgtgc aagaggagtt cgccgatgtg      720
ccagacgaac acggcgcgtt ccagctagat ttccccggcc acgtgtacgc ggtgtgtacc      780
gccagccaga acgcacatct tgacagccac atctccgtac tcgggacaga gggcaaggtc      840
cgcgtcgaac cggccttcta cccctgggac gaccgcgcgc tccagttgtc tcacgagggg      900
acgacggtcg agatcgactt cgaacagatc gaccagatgg aagaggagtt cgagtacttc      960
gcccactgcc tgctgaccga cactgagccc tacgccgacg gcgaacacgg cctcgtcgat     1020
atcaacacga tcaagtccgt ctacgaagca tccgagacgg agtcgacagt cagactcgat     1080
tga                                                                   1083
```

```
<210> SEQ ID NO 3
<211> LENGTH: 747
<212> TYPE: DNA
<213> ORGANISM: Caulobacter crescentus

<400> SEQUENCE: 3
atgtcctcag ccatctatcc cagcctgaag gcaagcgcg tcgtcatcac cggcggcggc        60
tcgggcatcg gggccggcct caccgccggc ttcgcccgtc agggcgcgga ggtgatcttc       120
ctcgacatcg ccgacgagga ctccagggct cttgaggccg agctggccgg ctcgccgatc       180
ccgccggtct acaagcgctg cgacctgatg aacctcgagg cgatcaaggc ggtcttcgcc       240
gagatcggcg acgtcgacgt gctggtcaac aacgccggca tgacgaccg ccacaagctg        300 gccgacgtga ccggcgccta tgggacgag cggatcaacg tcaacctgcg ccacatgctg        360
ttctgcaccc aggccgtcgc gccgggcatg aagaagcgtg gcggcgggc ggtgatcaac        420 ttcggttcga tcagctggca cctggggctt gaggacctcg tcctctacga aaccgccaag       480
gccggcatcg aaggcatgac ccgcgcgctg gcccgggagc tgggtcccga cgacatccgc       540
gtcacctgcg tggtgccggg caacgtcaag accaagcgcc aggagaagtg gtacacgccc       600
gaaggcgagg cccagatcgt ggcggcccaa tgcctgaagg gccgcatcgt cccggagaac       660
gtcgccgcgc tggtgctgtt cctggcctcg gatgacgcgt cgctctgcac cggccacgaa       720
tactggatcg acgccggctg gcgttga                                           747

<210> SEQ ID NO 4
<211> LENGTH: 1101
<212> TYPE: DNA
<213> ORGANISM: Caulobacter crescentus

<400> SEQUENCE: 4
atggaaacga tcagcaagag aagccttctc gccgcgggtc tggcggccgg cgtcgccgga       60
ctgccgcgcg cgccttcgc cgctcagccg ggccgcaagc tgggctatgc gatcctgggc       120
ctgggctact acgccacgcg catcatcatg ccgcgctttg ccgagtgcga gcactcgcgc       180
ctagccgccc tggtcagcgg tacgcccgaa aagctgaaaa cctacggcga gcagtacggg      240
atccccgaga cgcaccgcta cagctacgag accttcgacc ggatcatcga taatcccgat       300
gtcgacatcg tctatgtgat cacgcccaac agcctccacc gcccttcac cgagcgggcc        360 gccagggccg gcaagcacgt gatgtgcgaa agccgatgg cgaacacggt cgccgactgc        420
gaggcgatga tcgccgcctg caagaaggcc ggccgcaagc tgatgatcgg ctatcgcagc       480
cgcttccagg cccacaatat cgaagcgatc aagctggtgc gcgacggcgc gctgggaccg       540
gtgcgcacgg tggtcaccga tcacggcttc acgatcggcg atcccaagca gtggcgtttg       600
aacagggcgc tggccggcgg cggcagcctg atggacatcg catctacag cctgaacgcc        660 gcgcgctatc tcacgggcga ggagcctgtg gccgtcaacg ccgtggagtc cacggaccga       720
tccgatccgc gcttcggtga ggtggaggac atcatcaact tccagctcct cttcccatcc       780
ggcgccacgg ccaactgcgt gtcggcctac agcgtcaact gcaaccgcta tcgggtgagc       840
gggcccaagg gctgggtcga gatcgacccg gcgaccagct atcagggcca ggccatgcgg       900
gcgcagcttg gcggtccgcc cgcgccgcgt gaaccggcgc gcagcccaa gaaccagttc        960 tcggcccagc tggatcacct gtccgagtgc atcctcaccg gccgcgagcc gatcgtcggc      1020
ggggacgatg gcctcaagga cctccgagtg atcgaagcga tctaccgcgc ggcgcgagaa      1080
gggcggacgg tcaagctgtg a                                                1101
```

```
<210> SEQ ID NO 5
<211> LENGTH: 1008
<212> TYPE: DNA
<213> ORGANISM: pig

<400> SEQUENCE: 5
atggcgcttc gctggggcat cgtgtcagcc ggccttatct ccagcgactt cacgacggtg      60
ctgcggctgc tgcctcgctc tgagcaccag gtggtggcgg tagcggcccg ggatctgagc     120
cgggcaaagg agtttgcgcg gaaacacgac atccccaagg cctatggctc ctatgaggaa     180
ctggccaagg acccgaacgt ggaggtggcc tatattggca cccagcaccc ccagcacaag     240
gccacggtgt tgctttgcct ggcagctggc aaggccgtgc tgtgcgagaa gcccatgggc     300
gtgaacgccg cggaagtgcg tgaaatggtt gccgaggccc gatcccgagg cctcttccta     360
atggaggcca tctggacccg cttctttcct gctgtagagg ctctgaggtc tgttctggcc     420
caggaaactc tggggaccct acgagtggtt caggcaaatt tgggaagag tatcgccaat      480 gtaccccgat ccgtagactg ggcccaggct ggaggtagct tgctagacct tggcatctac     540
tgcctccagt tcatctccat ggtctacggt gggcagaagc cagagaagat ctcggcggtg     600
ggaaggcgct atgaaacagg tgtggacgac acggtcagcg tgctactcca gtacccagga     660
ggggtccagg gcagcttcac ctgcagcatc acttcccagc tctccaatac agtctctgtg     720
agcggtacca agggcatggc ccagatcctc gaccctgct ggtgcccaac agagctggtg      780 gtgaagggg agcataagga gttcccactg ccctcagccc caggcgagga gttcaattat     840
acaaatggaa tggcatgtg ttacgaggcc aagcacgtcc gggaatgctt gaagaagggc      900
ctgaaggaaa gccctatgat tactctggct gaaagtgagc tcctggctga catccttgag     960
gaggtgagga aggctattgg agtcaccttc ccccaggata aatgctga                 1008

<210> SEQ ID NO 6
<211> LENGTH: 870
<212> TYPE: DNA
<213> ORGANISM: Caulobacter crescentus

<400> SEQUENCE: 6
atgaccgctc aagtcacttg cgtatgggat ctgaaggcca cgttgggcga aggcccgatc      60
tggcatggcg acaccctgtg gttcgtcgac atcaagcagc gtaaaatcca caactaccac     120
cccgccaccg gcgagcgctt cagcttcgac gcgccggatc aggtgacctt cctcgcgccg     180
atcgtcggcg cgaccggctt tgtcgtcggt ctgaagaccg ggattcaccg cttccacccg     240
gccacgggct tcagcctgct gctcgaggtc gaggacgcgg cgctgaacaa ccgccccaac     300
gacgccacgg tcgacgcgca aggccgtctg tggttcggca ccatgcacga cggggaagag     360
aacaatagcg gctcgctcta tcggatggac ctcaccggcg tcgcccggat ggaccgcgac     420
atctgcatca ccaacggccc gtgcgtctcg cccgacggca agaccttcta ccacaccgac     480
accctggaaa agacgatcta cgccttcgac ctggccgagg acggcctgct gtcgaacaag     540
cgcgtcttcg tgcagttcgc cctgggcgac gatgtctatc cggacggttc ggtcgtcgat     600
tccgaaggct atctgtggac cgccctgtgg ggcggtttcg gcgcggtccg cttctcgccg     660
caaggcgacg ccgtgacgcg catcgaactg cccgccccca cgtcaccaa gccctgcttc      720 ggcgggcctg acctgaagac cctctatttc accaccgccc gcaagggcct gagcgacgag     780
accctggccc agtacccgct ggccggcggt gtgttcgcgc ttccggtcga tgtggccggc     840
caaccccagc atgaggtccg ccttgtctaa                                     870
```

<210> SEQ ID NO 7
<211> LENGTH: 391
<212> TYPE: PRT
<213> ORGANISM: Trichoderma reesei

<400> SEQUENCE: 7

```
Met Ala Ser Gly Asn Pro Tyr Thr Leu Lys Trp Gly Ile Met Ala Thr
1               5                   10                  15
Gly Gly Ile Ala Glu Thr Phe Cys Lys Asp Leu Leu Cys Asn Pro Ala
            20                  25                  30
Ile Arg Gly Ala Asp Asp Val Arg His Glu Ile Val Ala Val Ala Ser
        35                  40                  45
Ser Ser Ser Ser Lys Arg Ala Glu Glu Phe Leu Gln Arg Ile Asp Gly
    50                  55                  60
Ala Phe Asp Ala Lys Thr Tyr Gly Ser Tyr Pro Glu Leu Val Ala Asp
65                  70                  75                  80
Pro Asn Val Asp Ile Val Tyr Val Ala Thr Pro His Ser His His Phe
                85                  90                  95
Gln Asn Thr Met Leu Ala Leu Glu Ala Gly Lys Asn Val Leu Cys Glu
            100                 105                 110
Lys Ala Phe Thr Val Thr Ala Ala Gln Ala Arg Lys Leu Val Glu Thr
        115                 120                 125
Ala Lys Ala Lys Lys Leu Phe Leu Met Glu Ala Val Trp Thr Arg Tyr
130                 135                 140
Phe Pro Leu Ser Ile Lys Ile Arg Glu Leu Ile Ala Ala Gly Glu Ile
145                 150                 155                 160
Gly Thr Val Phe Arg Thr Ile Ala Asp Leu Ser Ile Asn Ala Asn Ser
                165                 170                 175
Glu Gln Gly Gln Ala Leu Lys Phe Ala Asp Ser His Arg Met Val Asn
            180                 185                 190
Pro Asp Leu Ala Gly Gly Ala Thr Leu Asp Leu Gly Val Tyr Pro Leu
        195                 200                 205
Thr Trp Val Phe Gln Thr Leu Tyr His Leu Gln Pro Glu Glu Asp Lys
210                 215                 220
Glu Ala Pro Thr Val Val Ala Ser Ser Asn Lys Tyr Thr Thr Gly Ala
225                 230                 235                 240
Asp Glu Asn Thr Ala Ile Ile Cys Ser Phe Pro Arg His Asn Ser Ile
                245                 250                 255
Gly Ile Ala Ser Thr Thr Met Arg Ala Asp Thr Asp Pro Glu Lys Asp
            260                 265                 270
Thr Ile Pro Ala Val Arg Ile Gln Gly Ser Lys Gly Glu Ile Gln Val
        275                 280                 285
Phe Phe Pro Thr Tyr Arg Pro Leu Lys Tyr Lys Val Val Lys Thr Asn
290                 295                 300
Gly Glu Ala Gln Thr Val Asp Cys Pro Ile Pro Gly Asp Pro Ala Arg
305                 310                 315                 320
Lys Gly Ser Gly His Gly Met Phe Trp Glu Ala Asp Glu Cys Ala Arg
                325                 330                 335
Cys Leu Arg Asp Gly Lys Leu Glu Ser Ala Thr Leu Pro Trp Lys Glu
            340                 345                 350
Ser Ile Val Ile Met Glu Thr Met Glu Glu Ala Leu Arg Gln Gly Gly
        355                 360                 365
Val Thr Tyr Pro Glu Leu Ile Thr Thr Asp Val Tyr Asp Pro Lys Ser
```

```
                    370                 375                 380

Pro Leu Asn Thr Gly Asn Gln
385                 390

<210> SEQ ID NO 8
<211> LENGTH: 360
<212> TYPE: PRT
<213> ORGANISM: Haloarcula marismortui

<400> SEQUENCE: 8

Met Asn Val Asp Ala Leu Thr Gly Gly Phe Asp Arg Arg Asp Trp Gln
1               5                   10                  15

Glu Gln Thr Ala Thr Asp Asn Pro Val Arg Phe Ala Met Ile Gly Val
            20                  25                  30

Gly Trp Trp Thr Thr Glu Gln Ala Met Pro Ala Val Asp Ala Gly Asp
        35                  40                  45

Leu Cys Glu Thr Thr Val Leu Val Ser Ser Asp Arg Glu Lys Ala Ala
    50                  55                  60

Asp Val Ala Ala Asp Ser Glu Thr Val Glu His Ala Ile Thr Tyr Glu
65                  70                  75                  80

Glu Phe His Asp Gly Ala Ala Ser Asp Ala Tyr Asp Ala Val Tyr Ile
                85                  90                  95

Val Thr Pro Asn Ala Leu His Leu Pro Tyr Val Glu Thr Ala Ala Glu
            100                 105                 110

Leu Asp Lys Ala Ile Leu Cys Glu Lys Pro Met Glu Ala Thr Ile Glu
        115                 120                 125

Arg Ala Glu Arg Met Val Glu Val Cys Asp Glu His Asp Ala Thr Leu
    130                 135                 140

Met Ile Ala Tyr Arg Met His Thr Glu Pro Ala Val Arg Arg Ala Lys
145                 150                 155                 160

Asp Leu Ile Asp Glu Gly Tyr Ile Gly Glu Pro Leu Phe Val His Gly
                165                 170                 175

Asn Met Thr Glu Pro Ile Leu Glu Leu Val Pro Asp Pro Asp Gln Trp
            180                 185                 190

Arg Leu Asp Gly Glu Leu Ser Gly Gly Cys Ala Val Met Asp Ile Gly
        195                 200                 205

Ile Tyr Pro Leu Asn Thr Ser Arg Phe Leu Leu Asp Ala Asp Pro Val
    210                 215                 220

Ala Val Arg Gly Thr Val Ala Ser Val Gln Glu Glu Phe Ala Asp Val
225                 230                 235                 240

Pro Asp Glu His Gly Ala Phe Gln Leu Asp Phe Pro Gly His Val Tyr
                245                 250                 255

Ala Val Cys Thr Ala Ser Gln Asn Ala His Leu Asp Ser His Ile Ser
            260                 265                 270

Val Leu Gly Thr Glu Gly Lys Val Arg Val Glu Pro Ala Phe Tyr Pro
        275                 280                 285

Trp Asp Asp Arg Ala Leu Gln Leu Ser His Glu Gly Thr Thr Val Glu
    290                 295                 300

Ile Asp Phe Glu Gln Ile Asp Gln Met Glu Glu Phe Glu Tyr Phe
305                 310                 315                 320

Ala His Cys Leu Leu Thr Asp Thr Glu Pro Tyr Ala Asp Gly Glu His
                325                 330                 335

Gly Leu Val Asp Ile Asn Thr Ile Lys Ser Val Tyr Glu Ala Ser Glu
            340                 345                 350
```

```
Thr Glu Ser Thr Val Arg Leu Asp
        355                 360
```

<210> SEQ ID NO 9
<211> LENGTH: 248
<212> TYPE: PRT
<213> ORGANISM: Caulobacter crescentus

<400> SEQUENCE: 9

```
Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
        35                  40                  45

Arg Ala Leu Glu Ala Glu Leu Ala Gly Ser Pro Ile Pro Pro Val Tyr
    50                  55                  60

Lys Arg Cys Asp Leu Met Asn Leu Glu Ala Ile Lys Ala Val Phe Ala
65                  70                  75                  80

Glu Ile Gly Asp Val Asp Val Leu Val Asn Asn Ala Gly Asn Asp Asp
                85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
        195                 200                 205

Ala Gln Cys Leu Lys Gly Arg Ile Val Pro Glu Asn Val Ala Ala Leu
    210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245
```

<210> SEQ ID NO 10
<211> LENGTH: 366
<212> TYPE: PRT
<213> ORGANISM: Caulobacter crescentus

<400> SEQUENCE: 10

```
Met Glu Thr Ile Ser Lys Arg Ser Leu Leu Ala Ala Gly Leu Ala Ala
1               5                   10                  15

Gly Val Ala Gly Leu Pro Arg Gly Ala Phe Ala Ala Gln Pro Gly Arg
            20                  25                  30

Lys Leu Gly Tyr Ala Ile Leu Gly Leu Gly Tyr Tyr Ala Thr Arg Ile
        35                  40                  45

Ile Met Pro Arg Phe Ala Glu Cys Glu His Ser Arg Leu Ala Ala Leu
    50                  55                  60
```

```
Val Ser Gly Thr Pro Glu Lys Leu Lys Thr Tyr Gly Glu Gln Tyr Gly
 65                  70                  75                  80

Ile Pro Glu Thr His Arg Tyr Ser Tyr Glu Thr Phe Asp Arg Ile Ile
                 85                  90                  95

Asp Asn Pro Asp Val Asp Ile Val Tyr Val Ile Thr Pro Asn Ser Leu
            100                 105                 110

His Arg Pro Phe Thr Glu Arg Ala Ala Arg Ala Gly Lys His Val Met
        115                 120                 125

Cys Glu Lys Pro Met Ala Asn Thr Val Ala Asp Cys Glu Ala Met Ile
130                 135                 140

Ala Ala Cys Lys Lys Ala Gly Arg Lys Leu Met Ile Gly Tyr Arg Ser
145                 150                 155                 160

Arg Phe Gln Ala His Asn Ile Glu Ala Ile Lys Leu Val Arg Asp Gly
                165                 170                 175

Ala Leu Gly Pro Val Arg Thr Val Val Thr Asp His Gly Phe Thr Ile
            180                 185                 190

Gly Asp Pro Lys Gln Trp Arg Leu Asn Arg Ala Leu Ala Gly Gly Gly
        195                 200                 205

Ser Leu Met Asp Ile Gly Ile Tyr Ser Leu Asn Ala Ala Arg Tyr Leu
210                 215                 220

Thr Gly Glu Glu Pro Val Ala Val Asn Ala Val Ser Thr Asp Arg
225                 230                 235                 240

Ser Asp Pro Arg Phe Gly Glu Val Glu Asp Ile Ile Asn Phe Gln Leu
                245                 250                 255

Leu Phe Pro Ser Gly Ala Thr Ala Asn Cys Val Ser Ala Tyr Ser Val
            260                 265                 270

Asn Cys Asn Arg Tyr Arg Val Ser Gly Pro Lys Gly Trp Val Glu Ile
        275                 280                 285

Asp Pro Ala Thr Ser Tyr Gln Gly Gln Ala Met Arg Ala Gln Leu Gly
290                 295                 300

Gly Pro Pro Ala Pro Arg Glu Pro Ala Pro Gln Pro Lys Asn Gln Phe
305                 310                 315                 320

Ser Ala Gln Leu Asp His Leu Ser Glu Cys Ile Leu Thr Gly Arg Glu
                325                 330                 335

Pro Ile Val Gly Gly Asp Asp Gly Leu Lys Asp Leu Arg Val Ile Glu
            340                 345                 350

Ala Ile Tyr Arg Ala Ala Arg Glu Gly Arg Thr Val Lys Leu
        355                 360                 365

<210> SEQ ID NO 11
<211> LENGTH: 335
<212> TYPE: PRT
<213> ORGANISM: pig

<400> SEQUENCE: 11

Met Ala Leu Arg Trp Gly Ile Val Ser Ala Gly Leu Ile Ser Ser Asp
1               5                  10                  15

Phe Thr Thr Val Leu Arg Leu Leu Pro Arg Ser Glu His Gln Val Val
                20                  25                  30

Ala Val Ala Ala Arg Asp Leu Ser Arg Ala Lys Glu Phe Ala Arg Lys
            35                  40                  45

His Asp Ile Pro Lys Ala Tyr Gly Ser Tyr Glu Glu Leu Ala Lys Asp
        50                  55                  60

Pro Asn Val Glu Val Ala Tyr Ile Gly Thr Gln His Pro Gln His Lys
65                  70                  75                  80
```

```
Ala Thr Val Leu Leu Cys Leu Ala Ala Gly Lys Ala Val Leu Cys Glu
                85                  90                  95

Lys Pro Met Gly Val Asn Ala Ala Glu Val Arg Glu Met Val Ala Glu
            100                 105                 110

Ala Arg Ser Arg Gly Leu Phe Leu Met Glu Ala Ile Trp Thr Arg Phe
        115                 120                 125

Phe Pro Ala Val Glu Ala Leu Arg Ser Val Leu Ala Gln Glu Thr Leu
    130                 135                 140

Gly Asp Leu Arg Val Val Gln Ala Asn Phe Gly Lys Ser Ile Ala Asn
145                 150                 155                 160

Val Pro Arg Ser Val Asp Trp Ala Gln Ala Gly Gly Ser Leu Leu Asp
                165                 170                 175

Leu Gly Ile Tyr Cys Leu Gln Phe Ile Ser Met Val Tyr Gly Gly Gln
            180                 185                 190

Lys Pro Glu Lys Ile Ser Ala Val Gly Arg Arg Tyr Glu Thr Gly Val
        195                 200                 205

Asp Asp Thr Val Ser Val Leu Leu Gln Tyr Pro Gly Gly Val Gln Gly
    210                 215                 220

Ser Phe Thr Cys Ser Ile Thr Ser Gln Leu Ser Asn Thr Val Ser Val
225                 230                 235                 240

Ser Gly Thr Lys Gly Met Ala Gln Ile Leu Asp Pro Cys Trp Cys Pro
                245                 250                 255

Thr Glu Leu Val Val Lys Gly Glu His Lys Glu Phe Pro Leu Pro Ser
            260                 265                 270

Ala Pro Gly Glu Glu Phe Asn Tyr Thr Asn Gly Met Gly Met Cys Tyr
        275                 280                 285

Glu Ala Lys His Val Arg Glu Cys Leu Lys Lys Gly Leu Lys Glu Ser
    290                 295                 300

Pro Met Ile Thr Leu Ala Glu Ser Glu Leu Leu Ala Asp Ile Leu Glu
305                 310                 315                 320

Glu Val Arg Lys Ala Ile Gly Val Thr Phe Pro Gln Asp Lys Cys
                325                 330                 335

<210> SEQ ID NO 12
<211> LENGTH: 289
<212> TYPE: PRT
<213> ORGANISM: Caulobacter crescentus

<400> SEQUENCE: 12

Met Thr Ala Gln Val Thr Cys Val Trp Asp Leu Lys Ala Thr Leu Gly
1               5                   10                  15

Glu Gly Pro Ile Trp His Gly Asp Thr Leu Trp Phe Val Asp Ile Lys
            20                  25                  30

Gln Arg Lys Ile His Asn Tyr His Pro Ala Thr Gly Glu Arg Phe Ser
        35                  40                  45

Phe Asp Ala Pro Asp Gln Val Thr Phe Leu Ala Pro Ile Val Gly Ala
    50                  55                  60

Thr Gly Phe Val Val Gly Leu Lys Thr Gly Ile His Arg Phe His Pro
65                  70                  75                  80

Ala Thr Gly Phe Ser Leu Leu Glu Val Glu Asp Ala Ala Leu Asn
                85                  90                  95

Asn Arg Pro Asn Asp Ala Thr Val Asp Ala Gln Gly Arg Leu Trp Phe
            100                 105                 110

Gly Thr Met His Asp Gly Glu Glu Asn Asn Ser Gly Ser Leu Tyr Arg
```

```
            115                 120                 125
Met Asp Leu Thr Gly Val Ala Arg Met Asp Arg Asp Ile Cys Ile Thr
    130                 135                 140

Asn Gly Pro Cys Val Ser Pro Asp Gly Lys Thr Phe Tyr His Thr Asp
145                 150                 155                 160

Thr Leu Glu Lys Thr Ile Tyr Ala Phe Asp Leu Ala Glu Asp Gly Leu
                165                 170                 175

Leu Ser Asn Lys Arg Val Phe Val Gln Phe Ala Leu Gly Asp Asp Val
            180                 185                 190

Tyr Pro Asp Gly Ser Val Val Asp Ser Glu Gly Tyr Leu Trp Thr Ala
        195                 200                 205

Leu Trp Gly Gly Phe Gly Ala Val Arg Phe Ser Pro Gln Gly Asp Ala
    210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Thr Ala Arg Lys Gly
                245                 250                 255

Leu Ser Asp Glu Thr Leu Ala Gln Tyr Pro Leu Ala Gly Gly Val Phe
            260                 265                 270

Ala Val Pro Val Asp Val Ala Gly Gln Pro Gln His Glu Val Arg Leu
        275                 280                 285

Val

<210> SEQ ID NO 13
<211> LENGTH: 28
<212> TYPE: DNA
<213> ORGANISM: Artificial
<220> FEATURE:
<223> OTHER INFORMATION: primer

<400> SEQUENCE: 13
agatctacca tggcgtctgg aaacccctt                                          28

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
agatcttcta ctgattcccc gtgttga                                            27

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
tatagaattc tgcgggcatg atgtttcaac                                         30

<210> SEQ ID NO 16
<211> LENGTH: 28
<212> TYPE: DNA
<213> ORGANISM: Artificial
<220> FEATURE:
<223> OTHER INFORMATION: primer

<400> SEQUENCE: 16
```
tatacccggg aaatcatcgc gagcccct                                          28

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
tatacccggg atgtcgagca cgggtagtca                                        30

<210> SEQ ID NO 18
<211> LENGTH: 31
<212> TYPE: DNA
<213> ORGANISM: Artificial
<220> FEATURE:
<223> OTHER INFORMATION: primer

<400> SEQUENCE: 18
tatagaattc atgcaagcgg cagagtactt t                                      31

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
tatacccggg tgattgaggt gattggcgat                                        30

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
tatacccggg ttatcacgcg acggacat                                          28

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
tatagaattc acgcaagatc aaaagatggc                                        30

<210> SEQ ID NO 22
<211> LENGTH: 29
<212> TYPE: DNA
<213> ORGANISM: Artificial
<220> FEATURE:
<223> OTHER INFORMATION: primer

<400> SEQUENCE: 22
tatacccggg aaggtttgga ggggtaata                                         29

<210> SEQ ID NO 23
<211> LENGTH: 31
<212> TYPE: DNA

```
<213> ORGANISM: Artificial
<220> FEATURE:
<223> OTHER INFORMATION: primer

<400> SEQUENCE: 23
tatacccggg tagaccattc agctatgagt g                                  31

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
tatagaattc tttgaagaat ctggaggagc                                    30

<210> SEQ ID NO 25
<211> LENGTH: 59
<212> TYPE: DNA
<213> ORGANISM: Artificial
<220> FEATURE:
<223> OTHER INFORMATION: primer

<400> SEQUENCE: 25
gtaatataaa tcgtaaagga aaattggaaa tttttttaaag cagctgaagc ttcgtacgc   59

<210> SEQ ID NO 26
<211> LENGTH: 63
<212> TYPE: DNA
<213> ORGANISM: Artificial
<220> FEATURE:
<223> OTHER INFORMATION: primer

<400> SEQUENCE: 26
tttgttcata tcgtcgttga gtatggattt tactggctgg agcataggcc actagtggat   60
ctg                                                                 63

<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27
aaattggatc cagatgtctt cactggtta                                     29

<210> SEQ ID NO 28
<211> LENGTH: 29
<212> TYPE: DNA
<213> ORGANISM: Artificial
<220> FEATURE:
<223> OTHER INFORMATION: primer

<400> SEQUENCE: 28
catacggatc ctgagtatgg attttactg                                     29

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
```

-continued atggcctctc ccacagtaaa g                                         21

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
gaaaatagga gcgtagagtc                                           20

<210> SEQ ID NO 31
<211> LENGTH: 58
<212> TYPE: DNA
<213> ORGANISM: Artificial Sequence
<220> FEATURE:
<223> OTHER INFORMATION: primer

<400> SEQUENCE: 31
gatccccggg taccgagctc gaattcactg gccgtcgttt ctcacataac aattattg  58

<210> SEQ ID NO 32
<211> LENGTH: 59
<212> TYPE: DNA
<213> ORGANISM: Artificial Sequence
<220> FEATURE:
<223> OTHER INFORMATION: primer

<400> SEQUENCE: 32
ggttgtcgac ctgcagcgta cgaagcttca gctggcggcc cgccattgtt taaagtaac 59

<210> SEQ ID NO 33
<211> LENGTH: 57
<212> TYPE: DNA
<213> ORGANISM: Artificial Sequence
<220> FEATURE:
<223> OTHER INFORMATION: primer

<400> SEQUENCE: 33
gaagttatta ggtgatatca gatccactag tggcctatgc acaagaaagc tcttaac   57

<210> SEQ ID NO 34
<211> LENGTH: 57
<212> TYPE: DNA
<213> ORGANISM: Artificial Sequence
<220> FEATURE:
<223> OTHER INFORMATION: primer

<400> SEQUENCE: 34
tgcaggcatg caagcttggc gtaatcatgg tcatagctgt tatcaattgg tttgaac   57

<210> SEQ ID NO 35
<211> LENGTH: 57
<212> TYPE: DNA
<213> ORGANISM: Artificial Sequence
<220> FEATURE:
<223> OTHER INFORMATION: primer

<400> SEQUENCE: 35
gaagttatta ggtgatatca gatccactag tggcctatgc atttgtacaa ggccgtg   57

<210> SEQ ID NO 36
<211> LENGTH: 56
<212> TYPE: DNA

```
<213> ORGANISM: Artificial Sequence
<220> FEATURE:
<223> OTHER INFORMATION: primer

<400> SEQUENCE: 36
tgcaggcatg caagcttggc gtaatcatgg tcatagctgt aaccgataga tgcaag        56

<210> SEQ ID NO 37
<211> LENGTH: 57
<212> TYPE: DNA
<213> ORGANISM: Artificial Sequence
<220> FEATURE:
<223> OTHER INFORMATION: primer

<400> SEQUENCE: 37
gatccccggg taccgagctc gaattcactg gccgtcgttt ttgacggaga cgatgtg       57

<210> SEQ ID NO 38
<211> LENGTH: 56
<212> TYPE: DNA
<213> ORGANISM: Artificial Sequence
<220> FEATURE:
<223> OTHER INFORMATION: primer

<400> SEQUENCE: 38
ggttgtcgac ctgcagcgta cgaagcttca gctggcggcc caacgttaag aaaatg        56

<210> SEQ ID NO 39
<211> LENGTH: 60
<212> TYPE: DNA
<213> ORGANISM: Artificial Sequence
<220> FEATURE:
<223> OTHER INFORMATION: primer

<400> SEQUENCE: 39
tgcttaaatc tataactaca aaaacacat acaggaattc acaatgactg ctcaagttac     60

<210> SEQ ID NO 40
<211> LENGTH: 58
<212> TYPE: DNA
<213> ORGANISM: Artificial Sequence
<220> FEATURE:
<223> OTHER INFORMATION: primer

<400> SEQUENCE: 40
cttattcagt tagctagctg agctcgactc tagaggatcc cagatcttta aaccaatc     58
```

MANUFACTURE OF XYLONIC ACID

This is a National Phase Application filed under 35 U.S.C. §371 as a national stage of PCT/FI2010/050205, filed on Mar. 17, 2010, an application claiming the benefit under 35 U.S.C. §119 of Finnish Patent Application No. 20095278, filed on Mar. 18, 2009, the content of each of which is hereby incorporated by reference in its entirety.

FIELD OF THE INVENTION

The present invention relates to the use of genetically modified fungi to convert xylose into xylonic acid. Especially the invention relates to a microbiological method for producing xylonic acid. The xylose may be supplied as a pure sugar, or in the form of a hemicellulose hydrolysate. The invention further relates to a spent culture medium obtained in the process, and to genetically modified filamentous fungi useful in said process.

BACKGROUND

Organic acids have a long history of use as food additives, chelators, and dispersants and may also serve as platform chemicals, from which other useful chemicals are derived via simple chemical reactions. Currently many platform chemicals are derived from the petroleum industry, but as oil stocks become depleted it will be increasingly important to replace petroleum-derived chemicals with chemicals derived from alternative sources, such as plant biomass. Plant biomass is ligno-cellulosic and may contain a substantial fraction of xylose when it is hydrolysed.

The Sequence Listing submitted in text format (.txt) on Sep. 14, 2011, named "2081474US_ST25.txt", (created on Tuesday, Sep. 13, 2011, 30.3 KB), is incorporated herein by reference.

Xylonic acid, as an organic acid, can be used in similar applications as gluconic acid but differs somewhat in its specific properties WO03/78347 (Chun et al.). Several applications for xylonic acid have been described including use as a precursor for 1,2,4-butanetriol synthesis (Niu et al. 2003 J Am Chem Soc. 2003 Oct. 29; 125(43):12998-9. Microbial synthesis of the energetic material precursor 1,2,4-butanetriol. Niu W, Molefe M N, Frost J W.), use to improve absorption of Vitamin C, WO90/03167 (Richard), use as a clarifier for polyolefins, U.S. Pat. No. 5,302,643 (Millner et al.), dispersal of concrete, WO03/78347 (Chun et al.), reduction of acrylamide in food cooked under heat, US2004/131737 (Tomoda et al.), and use as a biopesticide, WO2006/032530 (Pujos). However, the development of applications for xylonic acid has been limited by the lack of commercial supply and limited methods for producing xylonic acid.

Xylonate can be produced in high yields from D-xylose by *Pseudomonas* and *Gluconobacter* species, especially *Pseudomonas fragi* and *Gluconobacter oxydans*. D-Xylose is converted to xylono-γ-lactone by periplasmic xylose dehydrogenase and the xylono-γ-lactone is subsequently hydrolyzed either spontaneously or enzymatically to yield xylonate. Pre-treated ligno-cellulosic waste biomass can be used to produce xylonate using *G. oxydans*, and the use of *Gluconobacter* and other bacterial species for the conversion of sugars in ligno-cellulosic hydrolysates to aldonic acids, including the conversion of xylose to xylonic acid, has been described in WO03/78347 (Chun et al.). The use of *G. oxydans* and *G. cerinus* in the conversion of aldoses other than glucose to aldonic acid has been described in JP2007/028917 (Oe et al.).

WO2005/068642 and WO2008/091288 describe methods of producing 1,2,4 butanetriol enantiomers from xylose or xylonic acid containing starting material inside a transformed host cell. If the starting material is xylose, it is first converted to xylonic acid by xylose dehydrogenase and then further converted into 1,2,4 butanetriol by three other enzymes. The produced xylonate is not excreted but channeled inside the cell to subsequent reaction in the 1,2,4 butanetriol pathway.

Xylose dehydrogenase is naturally expressed in at least some bacteria. The xylose dehydrogenases found in *Pseudomonas* and *Gluconobacter* species are actually glucose dehydrogenases, which convert many other sugars than xylose and glucose to corresponding acids. Thus if the medium contains many different sugars, like ligno-cellulosic hydrolysates do, *Gluconobacter* produces many different acids, which can be difficult to separate. This is of course a drawback when only one specific acid is desired. In addition, high concentrations of ligno-cellulosic hydrolysate inhibit the growth and xylonic acid production of bacterial strains, and dilution or pretreatment of the hydrolysate is needed. Further the bacteria are relatively acid sensitive i.e. they do not grow at low pH.

The production of xylonate from xylose using a glucose oxidase or filamentous fungi producing glucose oxidase has been described in WO03/078347 (Chun et al.). No fungal system for bioproduction of xylonic acid with xylose dehydrogenase has been described so far.

Xylose dehydrogenase activity has been found in some eukaryotic organisms including a number of fungi such as *Trichoderma viridea* (Kanauchi M & Bamforth C W, 2003 *J Inst Brew* 109:203-207) and *Pichia querquum* (Suzuki T & Onishi H, 1973. *Appl Microbiol* 25:850-852). A xylose dehydrogenase encoding gene has recently been cloned from *Trichoderma reesei* (sexual/perfect state *Hypocrea jecorina*), and deposited in GenBank as EF136590. The gene was cloned into yeast, which was grown on a synthetic medium containing D-glucose as carbon source (Berghäll et al. 2007. *FEMS Microbiol Lett* 277: 249-253). After growth the yeast cells were disrupted and enzyme activity was measured from extracts of the disrupted cells by monitoring the formation of NADPH from NADP$^+$ in the presence of D-xylose. The role of this enzyme was said to be unclear, because in *T. reesei* D-xylose is predominantly catabolised through a path with xylitol and D-xylulose as intermediates and the mould is unable to grow on D-xylonic acid. In some prokaryotic organisms D-xylose is catabolised using D-xylose dehydrogenase with D-xylonate as an intermediate. The D-xylose dehydrogenase of *T. reesei* was not believed to be part of such a pathway. Instead it was suggested that said dehydrogenase may play a role in the regeneration of the cofactor NADP$^+$ in the presence of D-xylose.

The xylose dehydrogenase from *T. reesei* uses NADP$^+$ as a co-factor. Other xylose dehydrogenases have been described which use both NADP$^+$ and NAD$^+$ as co-factors or primarily NAD$^+$.

Many fungi are able to convert xylose to xylitol. Conversion of xylose to xylitol, with or without subsequent metabolism of the xylitol, represents a competing reaction for the conversion of xylose to xylonic acid. It has previously been shown that xylose reductase activity can be reduced or eliminated by the deletion of xylose and/or aldose reductases such as GRE3 in *S. cerevisiae* or xyrA in *A. niger* (Träff K L, et al., 2001. Appl Environ Microbial. December; 67(12):5668-74; Hasper A A et al., 2000. Mol Microbiol. April; 36(1):193-200).

There is presently a need for an improved method for producing xylonic acid without the drawbacks of the previously described bacterial processes. The present invention meets this need. Fungal species are in many cases the preferred industrial production organisms because of their low nutrition requirements, easy handling (rigid cell wall, big cells), inhibitor tolerance (e.g. present in lignocellulose hydrolysates), potential GRAS (generally regarded as safe) status and long history of usage e.g. in baking, brewing and acid production industries.

The present invention now provides a method for the manufacture of xylonic acid, which is especially suited for the biorefinery concept i.e. utilization of biomass. The method may be carried out at low pH. A further advantage is that a high concentration of ligno-cellulosic hydrolysate can be used, which makes the method economic. The method is especially convenient in that the xylonic acid can be recovered directly from the spent culture medium, without the need to disrupt the cells first. Further the method is highly specific in that production of other non-desired acids is negligible.

SUMMARY OF THE INVENTION

Although a fungal xylose dehydrogenase has been identified, it was not known whether the cells were capable of transporting substrate into the cells and/or transporting reaction product outside the cells. It has now surprisingly been found out that a fungal host that is genetically modified to produce xylose dehydrogenase can be used in a method for bioconverting xylose to xylonic acid, which preferably is recovered directly from the medium without disrupting the cells. The xylose dehydrogenase used is a cytoplasmic enzyme, but the produced xylonic acid is being excreted outside the cells. This could not be predicted, because production of xylonate using bacteria involves primarily periplasmic rather than cytoplasmic enzymes. It was thus unclear whether or not xylonate would cross the cell membrane. Secretion of xylonate has not previously been shown. Toxicity of xylonate in the cytoplasm for the cell was also unknown.

The present invention is directed to a method for producing xylonic acid, said method comprising: a) providing a fungal host that is genetically modified to express a xylose dehydrogenase encoding gene, b) culturing said host in a xylose-containing medium to obtain xylonic acid, and c) recovering the resulting xylonic acid containing medium, and d) optionally isolating and purifying the xylonic acid from the medium.

The invention is further directed to a spent culture medium obtained from a cultivation of a fungal host that has been genetically modified to express a xylose dehydrogenase encoding gene, and cultured in a xylose-containing medium to produce extracellular xylonic acid. The xylose-containing medium is preferably a hemicellulose hydrolysate.

The invention is also directed to the use of a fungal host that has been genetically modified to express a xylose dehydrogenase encoding gene in a method for producing extracellular xylonic acid from a xylose containing medium, which preferably is a hemicellulose hydrolysate.

The invention is still further directed to a recombinant filamentous fungus that has been genetically modified to express a xylose dehydrogenase encoding gene. Said fungus is useful in the method according to the invention for producing xylonic acid.

Specific embodiments of the invention are set forth in the dependent claims. Other objects, details and advantages of the present invention will become apparent from the following drawings, detailed description and examples.

BRIEF DESCRIPTION OF THE DRAWINGS

FIG. 10 shows the production of xylonic acid by *S. cerevisiae* H3494 at pH 5.5.

FIG. 11 shows the production of xylonic acid by *S. cerevisiae* H3494 at pH 3.5.

FIG. 12 shows the production of xylonic acid by *S. cerevisiae* PR77 (a) and H3611 (b) at pH 5.5, with 5 g $l^{-1}$ ethanol added 53 h after inoculation.

DETAILED DESCRIPTION OF THE INVENTION

Figure 1:
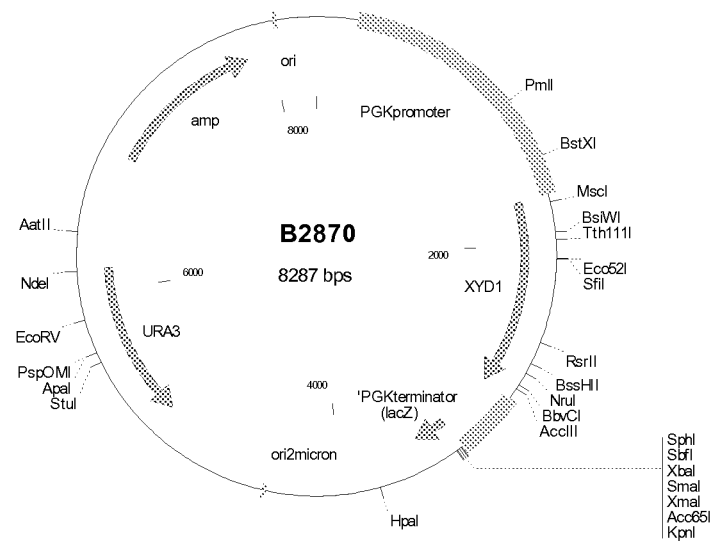
FIG. 1 is a diagrammatic representation of plasmid B2870, containing the XYD1 gene from *T. reesei* under control of the PGK1 promoter and terminator and the URA3 gene.

The invention relates to recombinant expression of exogenous or endogenous xylose dehydrogenase as a cytoplasmic enzyme in fungal species, enabling the host organism to convert xylose to xylonolactone, which is then further spontaneously or enzymatically hydrolysed to xylonate or xylonic acid. When an organic acid is described herein such as xylonic acid, the description also includes the anionic form of the acid i.e. xylonate, and vice versa. In practise it is often difficult to distinguish between the dissociated and non-dissociated form of the acid.

Briefly the present invention provides a method for producing xylonic acid (or xylonate) from xylose using recombinant organisms, which express an $NAD^+$ and/or $NADP^+$-dependent xylose dehydrogenase, with or without co-production of xylitol. One or more aldose or xylose reductase genes may be over-expressed for co-production of xylitol or other sugar alcohols such as arabitol or mannitol. Alternatively, aldose or xylose reductase genes can be deleted for reduced xylitol production. In addition, other genes may be over-expressed for co-production of xylonic acid and another organic acid, such as another sugar acid e.g. gluconic acid or galactonic acid, or alternatively deleted for reduced production of said other acids. A lactonase encoding gene may also be over-expressed to enhance conversion of xylonolactone to xylonate.

The metabolism of D-xylose is illustrated by the following reaction scheme:

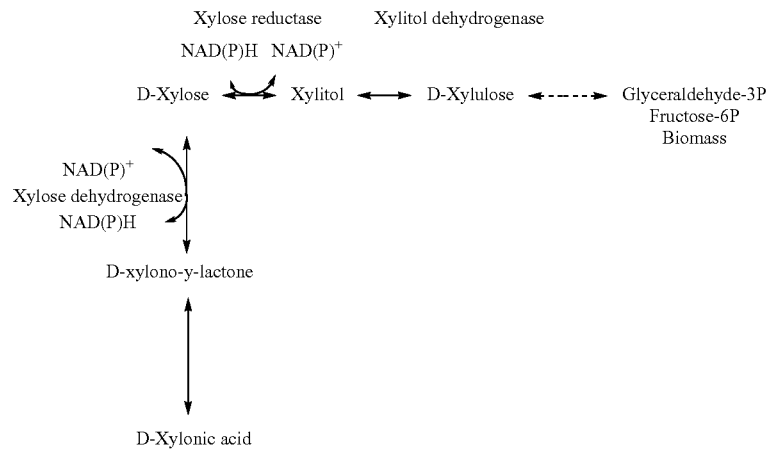

"Xylose dehydrogenase" as used herein refers to an enzyme that catalyses the conversion of D-xylose to D-xylonolactone. The enzyme is classified as EC 1.1.1.175 (an NAD$^+$-dependent xylose reductase), or EC 1.1.1.179 (NADP$^+$-dependent xylose dehydrogenase). Preferably the enzyme has a substantially greater specificity for xylose than glucose, and most preferably it is one that does not take part in pathways related to other sugar acids than xylonic acid. Several bacterial xylose dehydrogenases have higher activity with glucose than with xylose, but the T. reesei XYD1 is most active with xylose, showing only limited (11-25%) activity with D-glucose, D-galactose, L-arabinose or D-ribose. Pig liver xylose dehydrogenase (and other dimeric dihydrodiol dehydrogenases belonging to EC 1.1.1.179 and/or EC 1.3.1.20) oxidizes trans-dihydrodiols of aromatic hydrocarbons, several pentoses and hexoses, but of sugars use xylose as the substrate of preference (Zepeda S, Monasterio O, Ureta T. NADP(+)-dependent D-xylose dehydrogenase from pig liver. Purification and properties. Biochem J. 1990 Mar. 15; 266(3):637-44.)

"Xylose-containing medium" as used herein refers to a medium that comprises xylose in the form of a monomer or an oligomer. Preferably the medium is a "hemicellulose hydrolysate", which refers to a hemicellulose containing material that has been at least partially hydrolysed e.g. by acid, alkali or enzymatically. More preferably it is obtained from hydrolysis of lignocellulose, which is a complex plant material containing cellulose, hemicellulose and lignin, and most preferably it is a ligno-cellulosic hydrolysate rich in hemicellulose.

The following provides a detailed explanation of examples of the generation of recombinant, xylonate-producing fungi and the use of these organisms to produce xylonate. Fungus (adjective fungal) is used to refer to any organism belonging to the Kingdom Fungi, regardless of whether the organism grows primarily as yeast or as a filamentous organism. The term 'cell' may be used to refer to an individual yeast cell or to the compartment enclosed between the hyphal tip and a septum or between two septa of a filamentous fungus.

The genetically modified yeast or filamentous fungus used in the invention is made by performing certain genetic modifications to a host yeast cell or a filamentous fungal spore or cell.

A suitable host yeast or filamentous fungus is a fungus, which does not have the ability to consume xylose and convert it to biomass.

Another suitable host yeast or filamentous fungus is one which has the ability to transport xylose across its cell wall or membrane and the ability to grow naturally on xylose, such as one having an active natural pathway from xylose to xylulose-5-phosphate, which is further metabolized to fructose-6-phosphate and glyceraldehyde-3-phosphate.

Suitable hosts include, for example, yeast cells of the genera Saccharomyces, Kluyveromyces, Candida, Pichia, Pachysolen and Hansenula. Yeast species of particular interest include S. cerevisiae, S. exiguus, K. marxianus, K. lactis, K. thermotolerans, C. sonorensis, C. krusei (synonymous to Issatchenkia orientalis), C. shehatae, Pachysolen tannophilus and Pichia stipitis. S. cerevisiae, S. exiguus and C. krusei are examples of yeast which do not grow on xylose. K. tactis, K. matxianus, C. sonorensis, C. shehatae, P. tannophilus and P. stipitis are examples of yeast cells that grow on xylose. They have a natural xylose to xylulose-5-phosphate to fructose-6-phosphate and glyceraldehyde-3-phosphate pathway, natural functional aldose and/or xylose reductase genes, active xylitol dehydrogenase genes, and natural ability to transport xylose through the cell wall or membrane.

Suitable hosts also include, for example, filamentous fungi of the genera Aspergillus, Trichoderma, Monascus, and Penicillium. Fungal species of particular interest include A. niger, A. ficuum, A. phoenicis, T. reesei, T. harzianum, M. ruber, and P. chrysogenum. A. niger, A. ficuum, A. phoenicis, T. reesei, T. harzianum, M. ruber and P. chrysogenum are examples of fungi which grow on xylose.

Preferred hosts include those of the species S. cerevisiae, S. exiguus, K. mancianus, K. lactis, and A. niger.

The host organism contains genetic modifications and may contain other genetic modifications than those specifically described herein. Methods for making modifications of these types are generally well known and are described in various practical manuals describing laboratory molecular techniques. For example, the host cell is genetically modified to produce xylonic acid by addition of a xylose dehydrogenase encoding gene and may be genetically modified not to produce (or to produce) xylitol or ethanol, in addition to xylonic acid. Specific examples of such modifications include the deletion or disruption of aldose reductase encoding genes to prevent production of xylitol. These modifications may be present in the host cell prior to further modifying the host cell as described herein, or may be done simultaneously with or after such further modifications as described herein.

A host that is "genetically modified to express" includes embodiments, where a protein-encoding polynucleotide has been transformed into a host cell in such a manner that the host is capable of producing an active protein. The term also encompasses embodiments, where a promoter region has been modified in a host to allow the expression of a homologous gene.

"Aldose reductase" is an enzyme capable of catalysing the conversion of aldoses, including xylose, to sugar alcohols (e.g. xylitol), generally using NADPH as the reducing equivalent. "Xylose reductase" (XR) is an aldose reductase that has greatest specificity for the conversion of xylose to xylitol.

Genetically modified hosts used in the invention include a functional xylose dehydrogenase (XYD) encoding gene, that is preferably integrated into the genome of the host cell, but which may also be maintained on a self-replicating plasmid. Preferably the xylose dehydrogenase gene is derived from yeast, a filamentous fungus, an Archaean, a plant, a mammal, or a bacterium, preferably from *Trichoderma reesei, Haloarcula marismortui* or *Caulobacter crescentus*. "Derived from" in this connection means that the gene may be isolated from said microorganism source and optionally further modified. It may also be a synthetic version, where the codon usage may be optimized for expression in fungi. The term does not exclude minor modifications of the sequence e.g. by substitution, deletion, and/or insertion of one or a few nucleotides as long as the enzymatic activity of the encoded protein is retained.

Examples of suitable XYD genes include the Xyd1 gene from *Trichoderma reesei*, xylose dehydrogenase from Archaean *Haloarcula marismortui*, xylose dehydrogenase from the bacterium *Caulobacter crescentus* or potential xylose dehydrogenase—like polynucleotide sequences from *C. crescentus*, or dimeric dihydrodiol dehydrogenases from mammals that possess xylose dehydrogenase activity. The nucleotide sequence for the *T. reesei* Xyd1 gene is identified as SEQ ID NO: 1, the nucleotide sequence for the *H. marismortui* xylose dehydrogenase encoding gene is identified as SEQ ID NO: 2, the nucleotide sequence for the *C. crescentus* xylB is identified as SEQ ID NO: 3, the nucleotide sequence for the *C. crescentus* CC_1225 is identified as SEQ ID NO: 4 and the nucleotide sequence for the pig liver xylose dehydrogenase/dihydrodiol dehydrogenase encoding gene is identified as SEQ ID NO: 5. Deduced amino acid sequences for proteins produced by these XYD genes are identified as SEQ ID NO:s 7, 8, 9, 10 and 11, respectively. Suitable XYD genes include those that are at least 60%, 70%, 80%, 90%, 95%, 98% or 99% homologous to SEQ ID NO:s 1, 2, 3, 4 or 5. Suitable XYD genes include those that encode for enzymes that are at least 60%, 70%, 80%, 90%, 95%, 98% or 99% homologous to SEQ ID NO:s 7, 8, 9, 10 or 11.

Percent homology of amino acid sequences can conveniently be computed using BLAST version 2.2.1 software with default parameters. Sequences having an identities score and a positives score of a given percentage, using the BLAST version 2.2.1 algorithm with default parameters, are considered to be that percent identical or homologous. Particularly suitable xylose dehydrogenase genes include those that encode an enzyme that has an identities score of at least 60%, compared with SEQ ID NO: 1.

The XYD gene is under the control of a promoter and a terminator, both of which are functional in the modified fungal cell. As used herein, the term "promoter" refers to a sequence located upstream (i.e., 5') to the translation start codon of a structural gene and which controls the start of transcription of the structural gene. Similarly, the term "terminator" refers to a sequence located downstream (i.e., 3') to the translation stop codon of a structural gene and which controls the termination of transcription of the structural gene. A promoter or terminator is "operatively linked" to a structural gene if its position in the genome relative to that of the structural gene is such that the promoter or terminator, as the case may be, performs its transcriptional control function.

The use of native (to the host cell) promoters and terminators, together with respective upstream and downstream flanking regions, can permit the targeted integration of the XYD gene into specific loci of the host cell's genome, and for simultaneous integration of the XYD gene and deletion of a native gene, such as, for example, an aldose reductase (e.g. xyrA or GRE3) encoding gene.

The exogenous XYD gene may be maintained on a self-replicating plasmid, integrated randomly into the host cell's genome or inserted at one or more targeted locations. Examples of targeted locations include the locus of a gene that is desirably deleted or disrupted, such as the GRE3 gene in *S. cerevisiae* or the xyrA or xdhA genes in *A. niger*.

Targeted integration can be accomplished by designing a vector having regions that are homologous to the upstream (5'-) and downstream (3'-) flanks of the target gene. Either or both of these regions may include a portion of the coding region of the target gene. The XYD cassette (including suitable promoters and terminators if different from those of the target gene) and/or selection markers (with suitable promoters and terminators) will reside between the regions that are homologous to the upstream and downstream flanks of the target gene.

The genetically modified fungus may contain a single copy or multiple copies of the XYD gene. If multiple copies of the XYD gene are present, from 2 to 10 or more copies may be integrated into the genome, or >100 copies may be present on self-replicating plasmids. If multiple copies of the XYD gene are integrated into the genome, they may be integrated at a single locus (so they are adjacent each other), or at several loci within the host's genome. It is possible for different XYD genes to be under the control of different types of promoters and/or terminators.

Performance of the modified fungus is improved by making one or more additional modifications to its genome. These include one or more of (1) deletion or disruption of a xylose reductase (XR) encoding gene (XYL1 or other aldose reductase gene), (2) over-expression of a XR encoding gene (XYL1 or other aldose reductase gene) for co-production of xylitol, (3) addition or over-expression of a lactonase gene, (4) deletion of xylitol dehydrogenase encoding gene (xdhA or other xylitol dehydrogenase encoding gene).

Exemplary heterologous lactonases include xylonolactonase from *C. crescentus* and from other potential bacterial sources. The nucleotide sequence for the *C. crescentus* xylonolactonase xylC gene is identified as SEQ ID NO: 6. Deduced amino acid sequence for protein encoded by this gene is identified as SEQ ID NO: 12.

The host cell may contain one or more aldose reductase genes that produce enzymes that catalyze the conversion of xylose to xylitol. In one embodiment of this invention xylitol is co-produced with xylonate. Co-production occurs without further modification of the genome, or with addition of extra copies of the native xylose (aldose) reductase or a xylose (aldose) reductase from another organism, which may have more desirable properties. Co-production of xylonate and xylitol may be advantageous in particular embodiments, since most fungal xylose (aldose) reductases use NADPH as a cofactor, thus providing redox cofactors for NADP+ requiring xylose dehydrogenases such as that from *T. reesei*.

In another embodiment of this invention, xylonate is produced without co-production of xylitol (or with reduced xylitol production). One or more of the xylose (aldose) reductase genes may be disrupted or deleted. In general, the gene(s) selected for disruption or deletion are those which individually or collectively (1) account for at least 40%, preferably at least 50% of the host cell's xylose→xylitol reduction activity, and/or (2) are XR genes, i.e., genes that encode an enzyme specific to the xylose→xylitol reduction.

Exemplary xylose or aldose reductases, which may be over-expressed, or their genes deleted or disrupted to reduce xylitol accumulation or conversion of xylose to biomass comprise the GRE3 from *S. cerevisiae*, XYL1 from *K. lactis* and xyrA from *A. niger*.

By "delete or disrupt" a gene is meant that the entire coding region of the gene is eliminated (deletion), or the gene or its promoter and/or terminator region is modified (such as by deletion, insertion, or mutation) so that the gene encodes no active enzyme or encodes reduced levels of active enzyme. In the case of the XR or non-specific aldose reductase gene, a suitable method for accomplishing this is to clone the upstream and downstream flanking regions for the gene (which may include a portion of the coding region for the gene), produce a vector containing the cloned upstream and downstream flanks, and transform the host cell with the vector. The vector may contain other genetic material such as a marker gene or other gene (such as an XYD gene) that is desirably inserted into the genome of the host cell at the locus of the native XR or non-specific aldose reductase encoding gene.

Genetic modification of the host fungus is accomplished in one or more steps via the design and construction of appropriate vectors and transformation of the host fungus with those vectors. Electroporation, protoplast-PEG and/or chemical (such as calcium chloride- or lithium acetate-based) transformation methods can be used. The DNA used in the transformations can either be cut with particular restriction enzymes or used as circular DNA.

Useful vectors for genetic modification may contain the following components, in addition to a backbone portion (such as for propagation in *Escherichia coli* and conveniently obtained from commercially available yeast or bacterial vectors):

1. An XYD cassette (including promoter and terminator operatively linked to the gene), which may also be located between the 5'- and 3'-regions of the host cell xylose reductase or aldose reductase gene. The cassette may also have a selectable marker expression cassette, which may encode hygromycin or G418 resistance or uridine 5-phosphate or leucine biosynthetic enzymes.

2. Upstream (5'-) region of host cell xylose reductase or non-specific aldose reductase gene; marker expression cassette, host downstream (3'-) region of host xylose reductase or aldose reductase gene. The marker expression cassette may be a hygromycin or G418 resistance expression cassette with promoters and terminators, or a pyrG, URA3 or LEU2 expression cassette.

3. A xylitol production cassette consisting of 5' promoter, a xylose (aldose) reductase gene and 3' terminator. These may also be located between the 5'- and 3'-regions of the host cell xylose or aldose reductase gene.

4. A lactonase cassette containing 5' promoter, lactonase gene and 3' terminator.

5. Any of the foregoing plasmids further including a self-replication site that is active in the host cell.

All vectors can be circularized or linearized and may contain restriction sites of various types for linearization or fragmentation.

Specific XYD cassettes useful in the foregoing vectors include the *S. cerevisiae* PGK1 promoter, *T. reesei* XYD1 gene (or other described above), and ScPGK1, ScCYC1, ScGAL10 or KmPDC1 terminator. The XYD1 cassette for expression in *A. niger* includes glyceraldehyde-3-phosphate dehydrogenase (gpdA) promoter and anthranilate synthase component II (trpC) terminator, both from *Aspergillus nidulans*.

Specific xylitol production cassettes useful in the foregoing vectors include the *S. cerevisiae* PGK1 promoter, the *S. cerevisiae* GRE3 or the *A. niger* xyrA gene, and ScPGK1, ScCYC1, ScGAL10 or KmPDC1 terminator.

Typical selection marker genes encode proteins that (a) confer resistance to antibiotics or other toxins, e.g., zeocin (*Streptoalloteichus hindustanus* ble bleomycin resistance gene), G418 (kanamycin-resistance gene of Tn903), hygromycin (aminoglycoside antibiotic resistance gene from *E. coli*), ampicillin, tetracycline, or kanamycin for host cells; (b) complement auxotrophic deficiencies of the cell, such as amino acid leucine deficiency (LEU2 gene) or uridine deficiency (e.g. *S. cerevisiae* URA3 gene or pyrG gene in *A. niger*) or (c) confers ability for the cell to grow on a particular carbon or nitrogen source (e.g. amdS gene for growth on acetamide or acrylamide).

Successful transformants can be selected using the attributes contributed by the marker gene. Screening can be performed by PCR or Southern analysis to confirm that the desired insertions and deletions have taken place, to confirm copy number and to identify the point of integration of genes into the host cell's genome. Activity of the enzyme encoded by the inserted gene and/or lack of activity of enzyme encoded by the deleted gene can be confirmed using known assay methods.

The genetically modified fungus containing the XYD gene is useful to convert the pentose sugar xylose to xylonic acid or xylonate. Certain additional genetic modifications may be appropriate to enable the fungus to produce xylonic acid in acceptable yields, titres and/or productivity. For example, deletion of xylose or aldose reductases may be necessary to reduce by-product (xylitol or biomass) formation, as discussed above. Alternatively or additionally a lactonase may need to be over-expressed to enhance conversion of the lactone to the acid.

In the production process of the invention, the fungus is cultivated in a growth and production medium that includes a pentose, especially xylose, xylan or other oligomer of xylose, and preferably also other carbon containing compounds to provide for growth and energy. The carbon substrates may be provided as pure substrates or from complex sources. The xylose containing sugars are suitably hydrolysates of plant biomass e.g. hemicellulose-containing biomass, such as ligno-cellulose. In addition, the medium may consist of or contain complex, poorly defined elements, such as would be present in relatively inexpensive sources like corn steep liquor or solids, or molasses. Other sugars of the fermentation medium are notably hexose sugars such as glucose, fructose, mannose, or galactose and oligomers of glucose such as maltose, maltotriose, isomaltotriose, starch or cellulose. In case of oligomeric sugars, it may be necessary to add enzymes to the fermentation broth in order to digest these to the corresponding monomeric sugar. The medium may also contain alternative carbon sources, such as ethanol, glycerol, acetate, L-arabinose or amino acids, most notably carbon sources which do not inhibit the uptake of xylose into the host fungus, or the carbon source should be supplied in a manner that inhibition of uptake does not occur, for example hexose-limited fed-batch or continuous culture.

The medium will typically contain nutrients required by the particular host, including a source of nitrogen (such as amino acids, proteins, inorganic nitrogen sources such as ammonia or ammonium salts), and various vitamins and minerals.

Other fermentation conditions, such as temperature, cell density, selection of nutrients, and the like are not considered to be critical to the invention and are generally selected to provide an economical process. Temperatures during each of the growth phase and the production phase may range from above the freezing temperature of the medium to about 50° C., although the optimal temperature will depend somewhat on the particular microorganism. A preferred temperature, particularly during the production phase, is from about 25 to 30° C.

The pH of the process may or may not be controlled to remain at a constant pH, but should be between 3.0 and 6.5, depending on the production organism. Optimally the pH is controlled to a constant pH of 3.5 to 5.5. Suitable buffering agents are basic materials that neutralize xylonic acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here. It is within the scope of the invention, however, to allow the pH of the fermentation medium drop from a starting pH that is typically 6 or higher, to below the pKa of the acid fermentation product, such as in the range of about 3 to about 4.

The fermentation is conducted aerobically or microaerobically. If desired, specific oxygen uptake rate can be used as a process control. The process of the invention can be conducted continuously, batch-wise, or some combination thereof.

During the fermentation xylonic acid is excreted out from the cells into the growth medium from which it may be recovered without disrupting the cells.

"Spent culture medium" as used herein refers to the growth medium after fermentation with the genetically modified host cell. The spent culture medium containing the xylonic acid may be used as such e.g. as an additive in cement, but preferably the cells are first removed from the medium, preferably without disruption. The removed cells may in principle be reused. The cell-free medium containing the xylonic acid may be used as such as a xylonic acid containing source, or the xylonic acid may be isolated and purified there from using known methods such as ion exchange. Xylonic acid has similar properties as a chelator or dispersant to gluconic acid, which is widely used in the chemical industry. Further, xylonic acid or its derivatives may be used as a precursor, e.g. in polymerization reactions and for 1,2,4-butanetriol production.

The following examples are provided to illustrate the invention, but are not intended to limit the scope of the invention. It should be understood, however, that the embodiments given in the description above and in the examples are for illustrative purposes only, and that various changes and modifications are possible within the scope of the claims.

Example 1A

Construction of a *S. Cerevisiae* Strain Able to Produce Xylonic Acid (Self-Replicating Plasmids)

Figure 2:
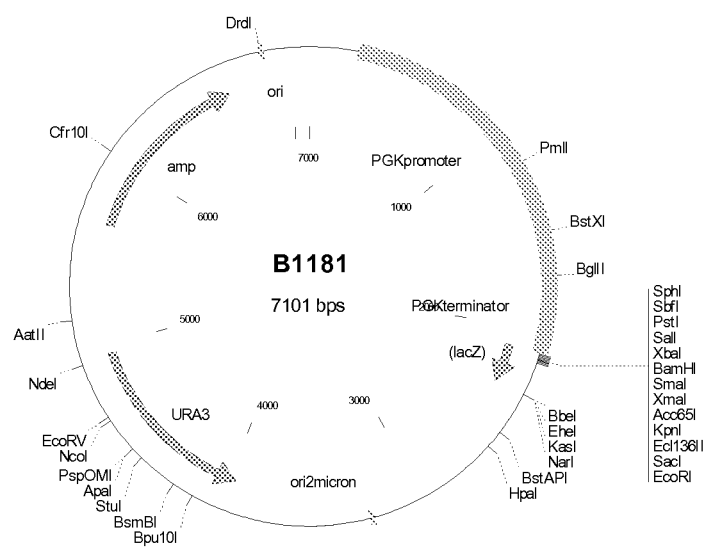
FIG. 2 is a diagrammatic representation of plasmid B1181, containing the URA3 gene.
Figure 3:
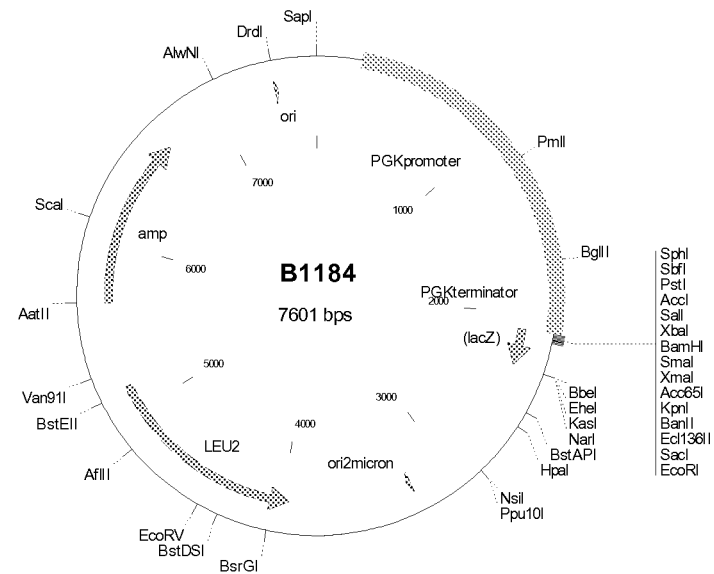
FIG. 3 is a diagrammatic representation of plasmid B1184, containing the LEU2 gene.

Plasmid B2870 (FIG. 1), containing the XYD1 gene encoding the *Trichoderma reesei* xylose dehydrogenase between the *S. cerevisiae* PGK1 promoter and terminator, was constructed using standard molecular biology methods. The XYD1 gene was amplified from a *T. reesei* cDNA library using PCR primer XYD1-a (SEQ ID NO: 13) and XYD1-b (SEQ ID NO: 14). The resulting fragment was ligated into the BglII site between the PGK1 promoter and terminator of YEplac195+PGK1PT (B1181, FIG. 2), generating plasmid B2870. Plasmid B2870 was introduced to *Saccharomyces cerevisiae* CEN.PK2-1D to generate strain H3494. Plasmid B2870 together with vector YEplac181+PGK1PT (B1184, FIG. 3), were introduced to *S. cerevisiae* CEN.PK2-1D by transformation to generate strain PR77. The PGK1 promoter and terminator (PGK1PT) of B1181 and B1184 was derived from vector pMA91 as HindIII fragment and cloned to HindIII site of vectors YEplac195 and YEplac181, respectively. Plasmid B2870 (XYD1) conferred the ability to grow in the absence of uracil and B1184 conferred the ability to grow in the absence of leucine to the strain.

Figure 4:
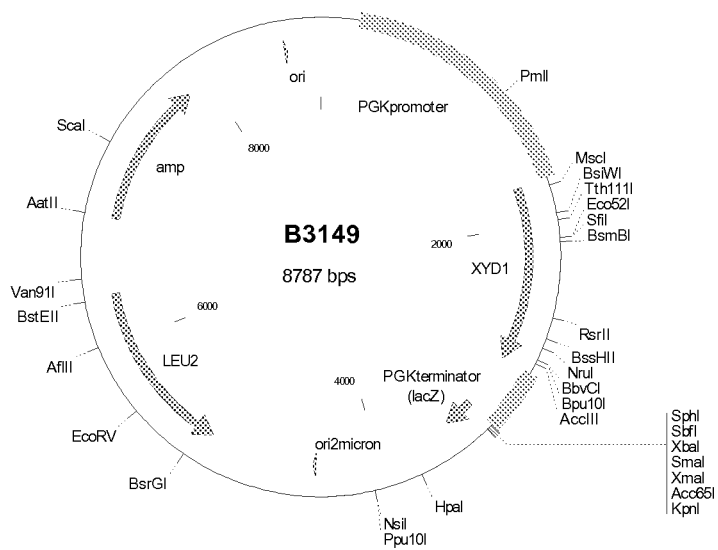
FIG. 4 is a diagrammatic representation of plasmid B3149 containing the LEU2 gene and the XYD1 gene from *T. reesei* under control of the PGK1 promoter and terminator.

In another construct the XYD1 gene encoding the *T. reesei* xylose dehydrogenase was digested from vector B2870 with BglII and the fragment was ligated into the BglII site between the PGK1 promoter and terminator of YEplac181+PGK1PT (B1184, FIG. 3), generating plasmid B3149 (FIG. 4). Plasmid B3149 was introduced to *S. cerevisiae* CEN.PK2-1D along with plasmid B1181 (FIG. 2), which was derived from YEplac195 with the PGK1 promoter and terminator, but with no gene insert. This generated strain H3611. H3611 is comparable to PR77, with the exception that the plasmid containing the XYD1 gene, B3149, conferred ability to grow in the absence of leucine and B1181 (empty vector) conferred the ability to grow in the absence of uracil to the strain, whereas in PR77 the plasmid containing the XYD1 gene conferred the ability to grow in the absence of uracil. Yeast transformations were carried out with the Gietz lab transformation kit (Medicorp Inc., Montrèal, Canada).

Example 1B

Construction of a *S. Cerevisiae* Strain Able to Produce Xylonic Acid (Integrated Cassettes)

Plasmids such as those described in Example 1A can be linearised using restriction digestion enzymes, in such a way that the 2 micron sequence (or autonomously replicating sequence, ARS, if appropriate) is deleted from the fragment containing the XYD1 expression cassette and selectable marker (e.g. LEU2 or URA3). These linearised fragments are then used to transform *S. cerevisiae*, with the result that the fragment is integrated into the genome. Integration may be random, or may also occur at a location for which there is homologous sequence present on both the fragment and in the genome (e.g. the PGK1 promoter or terminator or the URA3 gene in a fragment from B2870). The plasmids may also be modified to include specific sequences for targeted integration into the genome at the site of a specific gene, such as GRE3.

Example 2

Construction of a *Kluyveromyces Lactis* Able to Produce Xylonic Acid

Figure 5:
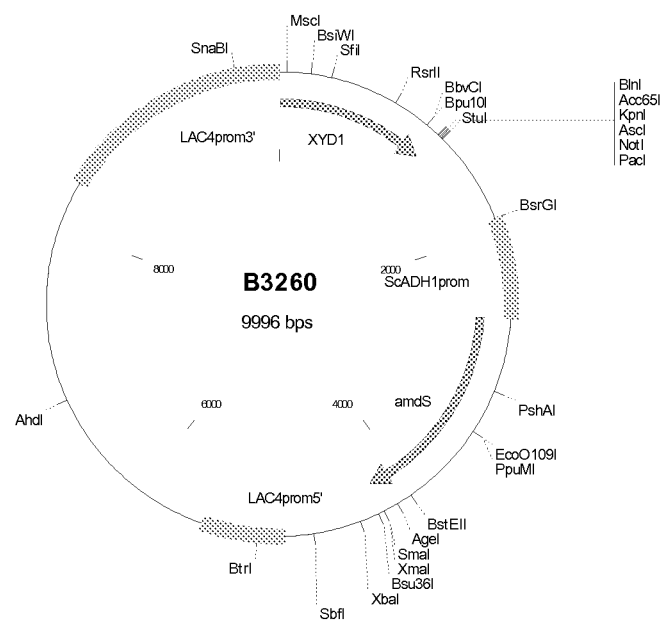
FIG. 5 is a diagrammatic representation of plasmid B3260 containing the AmdS gene and the XYD1 gene from *T. reesei* under control of the LAC4 promoter and terminator.

The XYD1 gene encoding the *T. reesei* xylose dehydrogenase was digested from vector B2870 with BglII, the fragment was made blunt ended and ligated into the pKLAC1 (Protein expression kit, New England Biolab, MA) vector digested with HindIII and BglII and made blunt end, generating plasmid B3260 (FIG. 5). Plasmid B3260 was digested with SacII and transformed to *Kluyveromyces lactis* GG799 strain (renamed as H3632) as instructed by the kit manufacturer. Transformants were selected by growth on acetamide containing plates and integration of the XYD1 gene was verified by PCR. Transformants were named as H3677 and H3678.

Example 3A

Figure 6:
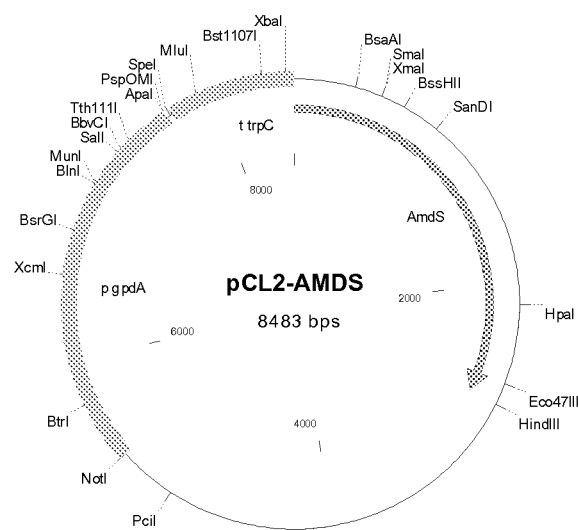
FIG. 6 is a diagrammatic representation of plasmid pCL2-AMDS for expression of genes in *A. niger*.
Figure 7:
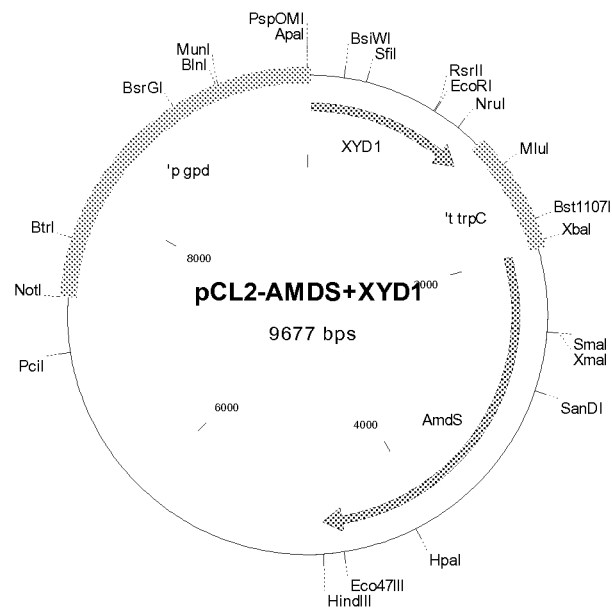
FIG. 7 is a diagrammatic representation of plasmid pCL2-AMDS+XYD1 for expression of the XYD1 gene in *A. niger*.

Construction of a Genetically Modified *A. Niger* Strain Able to Produce Xylonic Acid An *A. niger* expression plasmid containing the *T. reesei* XYD1 gene (pCL2-AMDS+XYD1; FIG. 7) was generated. The XYD1 gene was obtained by BglII digestion of plasmid B2870. The resulting fragment was ligated into to the SpeI site (filled in by Klenow DNA polymerase (NEB) and treated with Antarctic phosphatase (NEB)) of the pCL2 vector containing the *A. nidulans* amdS gene as a selection marker (FIG. 6). The resulting plasmid (FIG. 7) was then transformed into *A. niger* using standard methods for fungal transformation. The wild-type and the xyrA-Δ strain (described in Example 4C) were transformed. Transformants were selected for growth in the presence of acetamide as a sole nitrogen source. The transformants were verified by PCR.

Example 3B

Construction of Genetically Modified *Aspergillus Ficuum, Aspergillus Phoenicis, Trichoderma Reesei, Trichoderma Harzianum, Monascus Ruber*, and *Penicillium Chrysogenum* Strains, Which are Able to Produce Xylonic Acid A plasmid for expression (or over-expression in the case of *T. reesei*) of the *T. reesei* XYD1 gene in other filamentous fungi is produced by introducing the XYD1 gene between a suitable fungal promoter and terminator. The promoter and terminator may be the same as those used for transformation of *A. niger* (Example 3A), or may be specific to the organism to be transformed. The expression plasmid is introduced to the strain using standard methods for transformation of filamentous fungi and is expected to be integrated into the genome.

Optimally xylose reductase activity is reduced in the host strain by deletion of the corresponding xylose reductase encoding gene from those strains which possess an active gene (e.g. *A. ficuum, A. phoenicis, T. reesei, T. harzianum* and *P. chrysogenum*). A plasmid is generated for deletion of the xylose reductase encoding gene using the same approach outlined in Example 3A, but using sequences specific to the strain from which the gene is being deleted. Alternatively, for co-production of xylonate and xylitol, the xylitol dehydrogenase activity is reduced in the host strain by deletion of the corresponding xylitol dehydrogenase encoding gene from those strains which possess an active gene.

Example 4A

Construction of *S. Cerevisiae* Xylonic Acid Producing Strain with Reduced Xylitol Production The aldose reductase encoding gene GRE3 was disrupted by generating a disruption cassette by amplifying geneticin resistance gene from plasmid pUG6 (renamed B901) by using PCR primer GRE3del-a (SEQ ID NO: 21) and GRE3del-b (SEQ ID NO: 22). The resulting fragment was transformed to strain CEN.PK2-1D H2802 to generate strain H3613. Transformants were screened for the deletion of GRE3 by growth in the presence of geneticin and correct integration was verified with PCR and Southern blot. Plasmids B3149, containing the XYD1 gene and B1181 (empty vector) were introduced to strain H3613 using the Gietz lab transformation kit to generate strain H3622.

Example 4B

Construction of *Kluyveromyces Lactis* Xylonic Acid Producing Strain with Reduced Xylitol Production The xylose reductase encoding gene of *K. lactis* may be disrupted from strains producing xylonic acid described in Example 2. The xylose reductase encoding gene may be disrupted with a DNA fragment amplified from a plasmid (renamed B901) and conferring geneticin resistance by using suitable PCR primers, as described in Example 4A for disruption of the *S. cerevisiae* GRE3 gene.

The xylose reductase encoding gene of *K. lactis* was deleted by amplifying an upstream fragment (440 bp non-coding sequence+40 bp coding sequence) with primers KlXYL1p_1YE1 (SEQ ID NO:31) and KlXYL1p_2KMXp (SEQ ID NO:32) and a downstream fragment (290 bp of coding sequence+250 bp of non-coding sequence) with primers KlXYL1t_KMXt (SEQ ID NO:33) and KlXYL1t_YE2 (SEQ ID NO:34) using chromosomal DNA of strain H3632 as template. The primers contain an additional 40 bp sequence that is homologous to either vector Ye-plac195 or to a genenticin resistance marker. The amplified fragments were transformed together with the geneticin resistance marker from B901 digested with NotI and a vector Yeplac195 digested with BamHI and PstI into yeast strain FY834 renamed H3488. Due to homologous sequences at the ends of the fragments the fragments are recombined in vivo to form a yeast expression vector with the genenticin resistance gene flanked by the upstream and downstream fragments of *K. lactis* XYL1 gene. The resulting plasmid B3469 was digested with SmaI and SphI to release a deletion cassette, which was subsequently transformed into *K. lactis* strain H3632. Correct transformants were verified by PCR and reduced growth on xylose plates and named H3765 and H3766.

Example 4C

Figure 8:
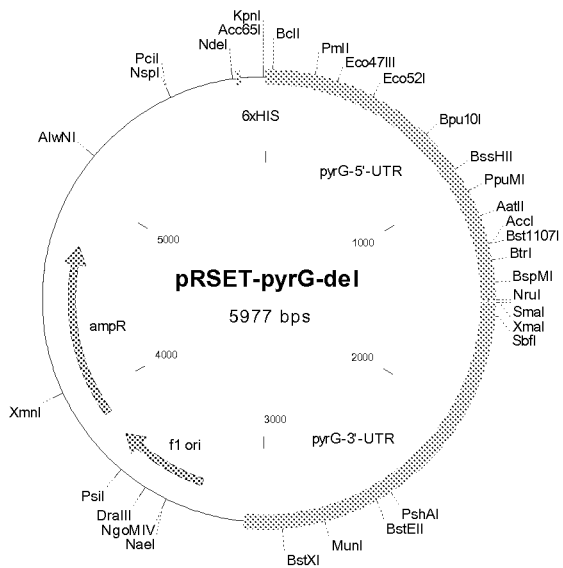
FIG. 8 is a diagrammatic representation of plasmid pRSET-pyrG-del, for deletion of the PyrG gene from *A. niger*.

Construction of *A. Niger* Xylonic Acid Producing Strain with Reduced Biomass Production Plasmid pRSET-pyrG-del (FIG. 8) contained 1500 bp (region −1700 . . . −201 from ATG start codon) from the *A. niger* pyrG promoter and 1560 bp (region +94 . . . +1653 from the stop codon) from the *A. niger* pyrG terminator. The pyrG promoter and terminator fragments were obtained by PCR of genomic DNA from *A. niger* ATCC1015 using primers pyrG-5-F+pyrG-5-R (for the promoter region) (SEQ ID NO:s 15 and 16, respectively) and pyrG-3-F_n+pyrG-3-R_n (for the terminator region) (SEQ ID NO:s 17 and 18, respectively) and the proofreading DNA polymerase Phusion (Finnzymes). Construction of the plasmid was performed in two steps. First, plasmid pRSET-A (Invitrogen) was digested with the restriction endonucleases EcoRI and PvuII (both NEB) and the terminator fragment (pyrG-3) by EcoRI (NEB). Ligation was performed using T4 DNA ligase (NEB) and the intermediary construct (pRSET-pyrG-3) was obtained. Second, pRSET-pyrG-3 was digested with the restriction endonucleases XmaI (NEB) and Ecl136II (Fermentas) and the promoter fragment (pyrG-5) by XmaI (NEB). Ligation was performed using T4 DNA ligase to generate construct pRSET-pyrG-del (FIG. 8).

A. niger ATCC1015 was transformed with plasmid pRSET-pyrG-del, which was digested by EcoRI (NEB) prior to transformation, using the standard fungal transformation methods and transformants were screened for integration of the plasmid at the pyrG locus by growth in the presence of 5-FOA. Deletion of the pyrG gene was confirmed by PCR with primers pyrG-del-F_n and pyrG-del-R_n (SEQ ID NO:s 19 and 20, respectively). Strain An1015_pyrGΔ was identified as a transformant in which pyrG had been deleted.

Figure 9:
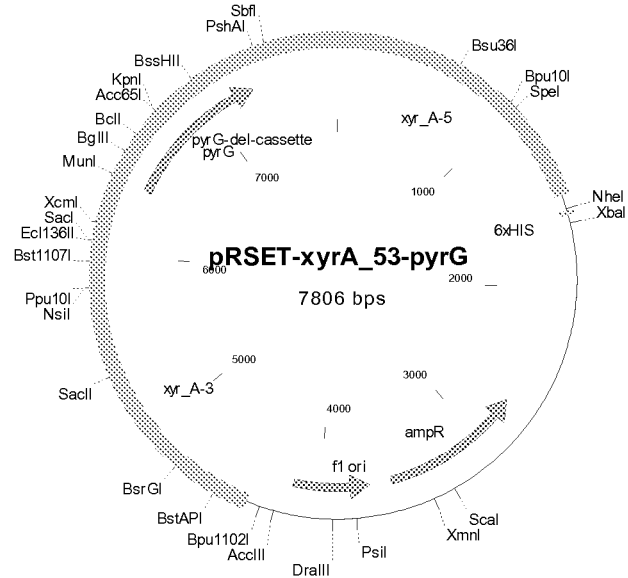
FIG. 9 is a diagrammatic representation of plasmid pRSET-xyrA_53-pyrG, for deletion of the XyrA gene from *A. niger*, using the PyrG gene as selection marker.

Plasmid pRSET-xyrA-53-pyrG (FIG. 9) contained 1492 bp (region −1581 . . . −90 from the ATG start codon) from the A. niger xyrA promoter, followed by the pyrG gene (including the native pyrG promoter and terminator regions, −500 . . . −1 from ATG and +1 . . . +497 from the stop codon, respectively) and 1500 bp from the A. niger xyrA terminator. The xyrA promoter and terminator fragments were obtained by PCR of genomic DNA from A. niger ATCC1015 using primers xyrA-5-F_n+xyrA-5-R_n (for the promoter region, SEQ ID NO:s 23 and 24, respectively) and xyrA-3-F+xyrA-3-R (for the terminator region, SEQ ID NO:s 25 and 26, respectively). The pyrG gene fragment was obtained by PCR of genomic DNA from A. niger ATCC1015 using primers pyrG-del-F_n+pyrG-del-R_n (SEQ ID NO:s 19 and 20, respectively). The proofreading DNA polymerase Phusion (Finnzymes) was used for all PCR reactions. Construction of the plasmid was performed in three steps. First, plasmid pRSET-A (Invitrogen) was digested by the restriction endonucleases EcoRI and PvuII (both NEB) and the terminator fragment (xyrA-3) by EcoRI (NEB). Ligation was performed using T4 DNA ligase and the intermediary construct pRSET-xyrA-3 was obtained. Second, pRSET-xyrA-3 was digested with the restriction endonucleases XmaI (NEB) and Ecl361II (Fermentas) and the promoter fragment (xyrA-5) by XmaI (NEB). Ligation was performed using T4 DNA ligase and the intermediary construct (pRSET-xyrA-53) was obtained. Third, pRSET-xyrA-53 was digested with the restriction endonuclease SmaI (NEB) and dephosphorylated by Antarctic phosphatase (NEB). The pyrG gene fragment was digested with the restriction endonuclease SmaI (NEB). Ligation was performed using T4 DNA ligase and the final construct pRSET-xyrA-53-pyrG was obtained (FIG. 9).

Strain An1015_pyrGΔ was transformed with plasmid pRSET-xyrA-53-pyrG, which was digested with EcoRI (NEB) prior to transformation, to generate strain An1015-xyrAΔ::pyrG. Transformation was performed using the standard fungal transformation methods and transformants were screened for integration of the deletion cassette at the xyrA locus by growth in the absence of uracil. Deletion of the xyrA gene was confirmed by PCR with primers: xyrA-ORF-F (SEQ ID NO: 29), xyrA-ORF-R (SEQ ID NO: 30). Strain An1015_xyrAΔ::pyrG was identified as a transformant in which the xyrA gene had been deleted. The strain produced less biomass from xylose than the parent strain. The XYD1 gene was integrated into the An1015-xyrAΔ::pyrG strain as described in example 3A.

Example 5A

Construction of a S. Cerevisiae Strain with Enhanced Co-Production of Xylonic Acid and Xylitol The S. cerevisiae aldose reductase GRE3 was overexpressed along with a XYD1 gene. When the xylose dehydrogenase uses $NADP^+$ as co-factor, such as the T. reesei xylose dehydrogenase, an aldose reductase which uses NADPH as co-factor should be used. By over-expressing an aldose reductase, regeneration of $NADP^+$ is facilitated and production of both products, xylonate and xylitol, is enhanced. The S. cerevisiae aldose reductase GRE3 was amplified from genomic DNA of S. cerevisiae strain W303-1B by using PCR primer GRE3-a (SEQ ID NO: 27) and GRE3-b (SEQ ID NO: 28). The resulting fragment was cloned into the BlgII site between PGK1 promoter and terminator in pMA91 vector, creating vector B1165. The plasmid B1165 was transformed to strain H3494, which contains the T. reesei XYD1 expressing plasmid B2870. Alternatively, xylose reductase from another organism, such as Candida tropicalis or Candida utilis, could be used.

Example 5B

Construction of a K. Lactis Strain with Enhanced Co-Production of Xylonic Acid and Xylitol When co-production of xylitol and xylonate from K. lactis (or any other fungus, either yeast or filamentous, which has a native pathway for conversion of xylose to biomass) is desired, the xylitol dehydrogenase (XDH) encoding gene is deleted, using a vector which contains sequences corresponding to the 5'-promoter and 3'-terminator regions of the XDH encoding gene, to allow accumulation of xylitol. In addition, a xylose reductase encoding gene may also be over-expressed. XYD1 or a similar xylose dehydrogenase encoding gene is over-expressed to enable production of xylonate with the xylitol.

The xylitol dehydrogenase encoding gene was deleted essentially as described in example 4B for the xylose reductase encoding gene. An upstream fragment (574 bp non-coding sequence) was amplified with primers KlXDHp1KMXt (SEQ ID NO:35) and KlXDHp2YE2 (SEQ ID NO:36) and a downstream fragment (118 bp of coding sequence+449 bp of non-coding sequence) with primers KlXDHt1YE1 (SEQ ID NO:37) and KlXDHt2KMXp (SEQ ID NO:38) using chromosomal DNA of strain H3632 as template. The resulting strains were named H3763 and H3764.

Example 5C

Construction of Genetically Modified Aspergillus Niger Strain or Other Filamentous Fungal Strains, that Co-Produce Xylonic Acid and Xylitol A plasmid for expression of the T. reesei XYD1 gene in A. niger is constructed by introducing the XYD1 gene between a suitable fungal promoter and terminator, as described in Example 3A. The expression plasmid is introduced to the strain using standard methods for transformation of filamentous fungi and is expected to be integrated into the genome. The xylitol dehydrogenase gene (xdhA and/or another gene (s) coding for xylitol dehydrogenase) is deleted using a similar strategy to the deletion of the xylose reductase gene (Example 4C), by preparing a deletion cassette in which the selection marker is flanked by sequence from the xdhA promoter and terminator and transformation of A. niger with the deletion cassette. The xylose reductase encoding gene is not deleted from these strains. In addition, the xylose reductase gene (xyrA) may also be over-expressed. XYD1 or a similar xylose dehydrogenase encoding gene is over-expressed to enable production of xylonate with the xylitol.

Example 6A

Production of Xylonic Acid by Strain H3494 at pH 5.5

H3494 was grown in modified synthetic complete (SC) medium lacking uracil (Sherman F, Fink G, Hicks J B. (1983) Methods in Yeast Genetics. A Laboratory Manual. Cold Springs Harbor Laboratory, Cold Springs Harbor, N.Y.). Glucose (10 g $l^{-1}$) was provided as the main carbon source, with 20 g xylose $l^{-1}$. Yeast was grown in 500 ml SC-ura medium in a Multifors bioreactor (max. working volume 500 ml, Infors HT, Switzerland) at pH 5.5, 30° C., 1 volume air [volume culture]$^{-1}$ min$^{-1}$ (vvm) and 500 rpm agitation with 2 marine impellors (4 blades). The pH was maintained constant by addition of 2 M NaOH or 1 M $H_2PO_4$. Silicone antifoaming agent (BDH, 0.2 ml $l^{-1}$) was added to prevent foam accumulation.

Extracellular metabolites in cell-free spent culture medium (xylonic acid, ethanol, glycerol, pyruvate and acetate), and glucose were analysed by HPLC on a Fast Acid Analysis Column (100 mm×7.8 mm, Bio-Rad, Hercules, Calif.) linked to an Aminex HPX-87H column (BioRad Labs) with 2.5 mM $H_2SO_4$ as eluent and a flow rate of 0.5 ml min$^{-1}$. The column was maintained at 55° C. Peaks were detected using a Waters 410 differential refractometer and a Waters 2487 dual wavelength UV (210 nm) detector. Xylonic acid concentrations were sometimes also measured using the hydroxymate method in which samples were diluted in 0.75 M HCl and heated at 100° C. to convert xylonic acid to xylonolactone before adding 50 µl of the diluted sample to 100 µl hydroxylamine reagent (2 M hydroxylamine HCl in 2 M NaOH). HCl (65 µl, 3.2 M) was added, followed by addition of 50 µl $FeCl_3$ (100 g $l^{-1}$ in 0.1 M HCl). Absorbance was measured immediately at 550 nm and xylonic acid concentration was determined by comparison with a standard curve.

H3494 produced extracellularly 2.7 g xylonate $l^{-1}$ after 144 h at pH 5.5 (Table 1, FIG. 10). Xylonate began to accumulate in the culture supernatant after the initial glucose supply had been either consumed or converted to ethanol. The xylonate production rate (33 mg xylonate $l^{-1}$ h$^{-1}$ or 10 mg xylonate [g biomass]$^{-1}$ h$^{-1}$) decreased after the ethanol had been consumed (13 mg xylonate $l^{-1}$ h$^{-1}$ or 3 mg xylonate [g biomass]$^{-1}$ h$^{-1}$; FIG. 10). The yield of xylonate on xylose was approximately 0.47 g xylonate [g xylose]$^{-1}$. In addition to xylonate, xylitol, glycerol and acetate were also produced. Glycerol and acetate were subsequently consumed, but the xylitol was not.

Example 6B

Production of Xylonic Acid by Strain H3494 at pH 3.5

H3494 was grown in SC medium lacking uracil (-ura). Glucose (10 g $l^{-1}$) was provided as the main carbon source, with 20 g xylose $l^{-1}$. Yeast was grown in 500 ml SC-ura medium in a Multifors bioreactor (max. working volume 500 ml, Infors HT, Switzerland) at pH 3.5, 30° C., 1 volume air [volume culture]$^{-1}$ min$^{-1}$ (vvm) and 500 rpm agitation with 2 marine impellors (4 blades). The pH was maintained constant by addition of 2 M NaOH or 1 M $H_2PO_4$. Silicone antifoaming agent (BDH, 0.2 ml $l^{-1}$) was added to prevent foam accumulation.

H3494 produced extracellularly 1.5 g xylonate $l^{-1}$ after 50 h at pH 3.5 (Table 1, FIG. 11), as analyzed from cell-free spent culture medium using the methods described in Example 6A. The xylonate production rate during growth on ethanol was 32 mg xylonate $l^{-1}$ h$^{-1}$ (7 mg xylonate [g biomass]$^{-1}$ h$^{-1}$), but xylonate production stopped after the ethanol had been consumed (FIG. 11). The yield of xylonate on xylose was approximately 0.47 g xylonate [g xylose]$^{-1}$.

In addition to xylonate, xylitol, glycerol and acetate were also produced. Glycerol and acetate were subsequently consumed, but the xylitol was not.

Example 7

Production of Xylonic Acid by Strains PR77 and H3611 at pH 5.5 with Additional Ethanol Since xylonate production occurred at the highest rates when ethanol was present as the carbon source, the production of additional xylonate with addition of extra ethanol was demonstrated. PR77 is the equivalent of H3494, but is able to grow in the absence of added leucine.

PR77 was grown in SC-ura medium, which also lacked leucine (-leu). Glucose (10 g $l^{-1}$) was provided as the main carbon source, with 20 g xylose $l^{-1}$. After approximately 50 h 5 g ethanol $l^{-1}$ was added to the culture. Yeast were grown in a Multifors bioreactor (max. working volume 500 ml, Infors HT, Switzerland) at pH 5.5, 30° C., 1 volume air [volume culture]$^{-1}$ min$^{-1}$ (vvm) and 500 rpm agitation with 2 marine impellors (4 blades). The pH was maintained constant by addition of 2 M NaOH or 1 M $H_2PO_4$. Silicone antifoaming agent (BDH, 0.2 ml $l^{-1}$) was added to prevent foam accumulation.

PR77 produced extracellularly 6.1 g xylonate $l^{-1}$ after 144 h at pH 5.5 when extra ethanol was supplied (Table 1 FIG. 12) analyzed from cell culture medium. Addition of ethanol resulted in higher volumetric and specific rates of xylonate production (52 mg xylonate $l^{-1}$ h$^{-1}$ or 12 mg xylonate [g biomass]$^{-1}$ h$^{-1}$, respectively) than without the extra ethanol. The yield of xylonate on xylose was approximately 0.57 g xylonate [g xylose]$^{-1}$. Xylitol was still the major by-product.

A similar strain was constructed, but with plasmids B3149 and B1181 instead of plasmids B2870 and B2159 (resulting in the XYD1 gene being carried on the plasmid conferring ability to grow in the absence of leucine, rather than the plasmid conferring ability to grow in the absence of uracil). H3611 produced 3.4 g xylonate $l^{-1}$ after 144 h at pH 5.5 with extra ethanol added (Table 2, FIG. 12). Xylonate was produced at a rate of 33 mg xylonate $l^{-1}$ h$^{-1}$ (7 mg xylonate [g biomass]$^{-1}$ h$^{-1}$). The yield on xylose was approximately 0.44 g xylonate [g xylose]$^{-1}$.

Example 8

Reduction in Xylitol Production for Xylonate Producing S. Cerevisiae

Strain H3622, with GRE3 deleted and containing XYD1, was grown in SC medium lacking leucine and uracil with 10 g glucose $l^{-1}$, 20 g xylose $l^{-1}$ and 5 g ethanol $l^{-1}$ added after approximately 50 h in 500 ml bioreactor cultures at pH 5.5, 30° C., 1 volume air [volume culture]$^{-1}$ min$^{-1}$ (vvm) and 500 rpm agitation with 2 marine impellors (4 blades).

Deletion of GRE3 in S. cerevisiae strains expressing the T. reesei XYD1 encoding xylose dehydrogenase resulted in xylitol production being reduced from 1.8 g xylitol $l^{-1}$ for H3611 to 0.6 g xylitol $l^{-1}$ for H3622 (Table 2). Xylonate production in H3622 was reduced to 2.0 g $l^{-1}$ (Table 2). Biomass and glycerol production were not affected by the deletion of GRE3 (Table 2). Xylitol production was reduced by 67%. The yield of xylonate on xylose was approximately 0.60 g xylonate [g xylose]$^{-1}$, compared with a yield of only 0.44 g xylonate [g xylose]$^{-1}$ for H3611.

Example 9

Production of Xylonic Acid by *K. Lactis* Strains H3677, H3678, H3763 and H3765

Strains H3677 and H3678 containing the XYD1 gene under *K. lactis* LAC4 promoter as well as the control strain without XYD1 (strain H3632) were cultured in Yeast Nitrogen Base (YNB) without amino acids medium (Difco) with 1% w/v galactose and 2% w/v xylose as carbon sources. The strains were cultured in 100 ml Erlenmeyer flasks in 50 ml medium with 100 rpm agitation at 30° C.

Figure 13:
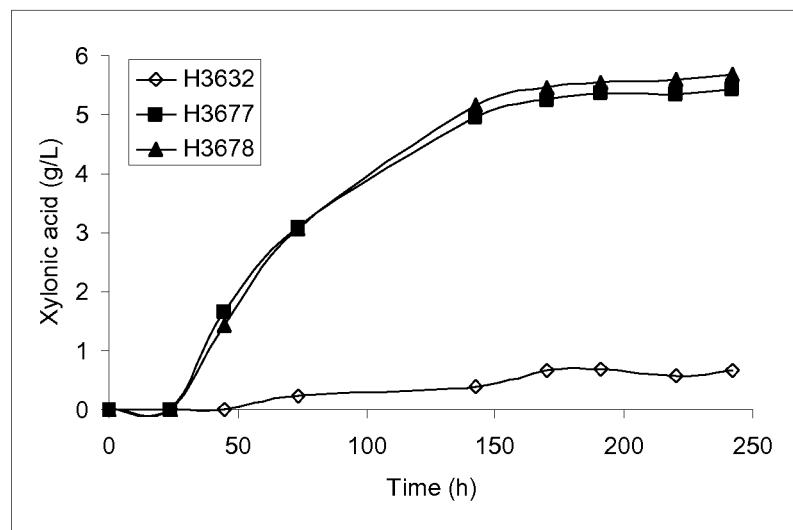
FIG. 13 shows the production of xylonic acid by *K. lactis* strains H3677 and H3678, and wt strain H3632.

The *K. lactis* strains expressing the XYD1 gene produced approximately 6.5 g xylonate l$^{-1}$ (FIG. 13). At the same time 9-12 g xylitol l$^{-1}$ was produced. When strain H3677 was grown in 1% w/v galactose and approximately 4% w/v xylose, 16 to 21 g xylonate l$^{-1}$ was produced at a rate of 0.16 g l$^{-1}$ h$^{-1}$, and only 3 to 5 g xylitol l$^{-1}$ was produced as by-product.

When *K. lactis* H3765, from which the xylose reductase had been deleted, was grown in 1% w/v galactose and 2% w/v xylose, 8.0±0.8 g xylonate l$^{-1}$ were produced at a rate of 0.13 g l$^{-1}$ h$^{-1}$. Less than 0.4 g xylitol l$^{-1}$ was produced. *K. lactis* H3763, from which the xylose dehydrogenase had been deleted, produced 2.0±0.1 g xylonate l$^{-1}$ with 14.4±0.5 g xylitol l$^{-1}$ when grown under the same conditions.

Example 10

Production of Xylonic Acid by *A. Niger* Strains

*A. niger* ATCC1015+XYD1 and *A. niger* ATCC1015ΔxyrA+XYD1 were grown in YNB without amino acids medium with 50 g xylose l$^{-1}$ as carbon source. Pre-cultures were grown in medium containing 10 g yeast extract l$^{-1}$, 20 g peptone l$^{-1}$ and 30 g gelatine l$^{-1}$ (50 ml medium in 250 ml flasks). Mycelium from 50 ml cultures was collected by filtration, washed with sterile H$_2$O and re-suspended in 50 ml production medium (YNB+50 g xylose l$^{-1}$) in 250 ml flasks. Cultures were incubated at 30° C., 200 rpm. Culture supernatant was analysed by HPLC.

*A. niger* ATCC1015+XYD1 produced 0.7 g xylonic acid l$^{-1}$ extracellularly in 48 h. *A. niger* ATCC1015 (wild-type) produced no xylonic acid when grown under the same conditions. *A. niger* ATCC1015ΔxyrA+XYD1 produced 1.7 g xylonic acid l$^{-1}$ extracellularly in 72 h. The parent strain (*A. niger* ATCC1015ΔxyrA) produced no xylonic acid when grown under the same conditions.

Example 11

Co-Expression of a Lactonase Encoding Gene with a Xylose Dehydrogenase

Production of xylonate could be enhanced by introducing a lactonase gene, such as xylC (CC_0820) from *C. crescentus* (SEQ ID NO: 6), along with a xylose dehydrogenase gene such as XYD1. The lactonase will enhance the rate at which xylonolactone is converted to xylonate at cytosolic pH. Expression cassettes are constructed with the lactonase gene under control of a suitable promoter. The xylose dehydrogenase encoding gene may be introduced as described in examples 1A, 1B, 2 or 3A.

A codon optimized synthetic gene of *C. crescentus* lactonase xylC (CC_0820) (SEQ ID NO: 6) was obtained from Gene Art (Germany). The gene was cloned under the TPI1 promoter in vector B2158 with homologous recombination. B2158 was derived from pYX242 (R&D Systems, UK) by removal of the ATG and HA-tag from the multiple cloning site with EcoRI-XhoI digestion and addition of an EcoRI-SalI linker region from pUC19. The XylC gene was amplified with primers recCC00820F (SEQ ID NO:39) and recCC00820R (SEQ ID NO:40) using the linear fragment obtained from Gene Art as a template. The primers contain a region of 40 bp homologous to vector B2158 digested with enzymes EcoRI and BamHI. The PCR amplified fragment and EcoRI and BamHI digested vector were transformed to yeast strain H3488 and selected for growth on plates lacking uracil. Plasmids were extracted and transformed into *E. coli* strain. Correct clones were verified by sequencing and restriction digestion. The resulting clones were named B3573 and B3574. B3573 was transformed into yeast strain H3698 expressing xylose dehydrogenase described in SEQ ID NO. 3 resulting in strain H3698+B3574, expressing both xylose dehydrogenase and lactonase.

A strain expressing both a lactonase gene CC0820 (SEQ ID NO: 6) and the xylose dehydrogenase described in SEQ ID NO. 3 produced 12.4 g xylonate l$^{-1}$ and only 0.6 g xylitol l$^{-1}$ in 52 h when grown at pH 5.5 as described in example 7. The production rate (0.24 g xylonate l$^{-1}$ h$^{-1}$) was higher than that of strain H3698 (0.16 g xylonate l$^{-1}$ h$^{-1}$), lacking the lactonase. The strain expressing both the lactonase and the xylose dehydrogenase (SEQ ID NO. 3) also produced xylonate at a higher rate (0.22 g l$^{-1}$ h$^{-1}$) than the strain lacking the lactonase (H3698; 0.08 g l$^{-1}$ h$^{-1}$) when the strains were grown at pH 3.

Example 12A

Production of Xylonate Using Alternative Xylose Dehydrogenase

In addition to the XYD1 gene from *T. reesei*, xylose dehydrogenase may be introduced to a strain by incorporating alternative xylose dehydrogenase genes, such as those described for *C. crescentus* (SEQ ID NO: 3), or *H. marismortui* (SEQ ID NO: 2) or similar sequences such as *C. crescentus* CC_1225 (SEQ ID NO: 4) or pig liver xylose dehydrogenase/dihydrodiol dehydrogenase encoding gene, which is identified as SEQ ID NO: 5. A codon optimized synthetic gene based on SEQ ID NO: 4 was obtained from Gene Art (Germany). The gene was ligated into the BglII site between the PGK1 promoter and terminator of YEplac195+PGK1PT (B1181, FIG. 2), as in example 1, generating plasmid B3353 and B3365 (individual clones). Plasmids B3353 and B3365 were separately introduced to *Saccharomyces cerevisiae* CEN.PK2-1D strain H2802 to generate strains H3679 and H3686, respectively. A control strain was created by introducing plasmid B1181 to *S. cerevisiae* CEN.PK2-1D H2802 to generate strain H3680.

Codon optimised synthetic genes based on SEQ ID No: 3 and SEQ ID NO: 5 were also obtained from Gene Art (Germany). These genes were ligated into BglII site between the PGK1 promoter and terminator of YEplac195+PGK1PT (B1181, FIG. 2), as in example 1, generating plasmids B3441 and B3443. These plasmids were introduced separately to *S. cerevisiae* CEN.PK2-1D strain H2802 to generate strains H3698 and H3700, containing the *C. crescentus* and the pig liver xylose dehydrogenase/dihydrodiol dehydrogenase genes, respectively.

Figure 14:
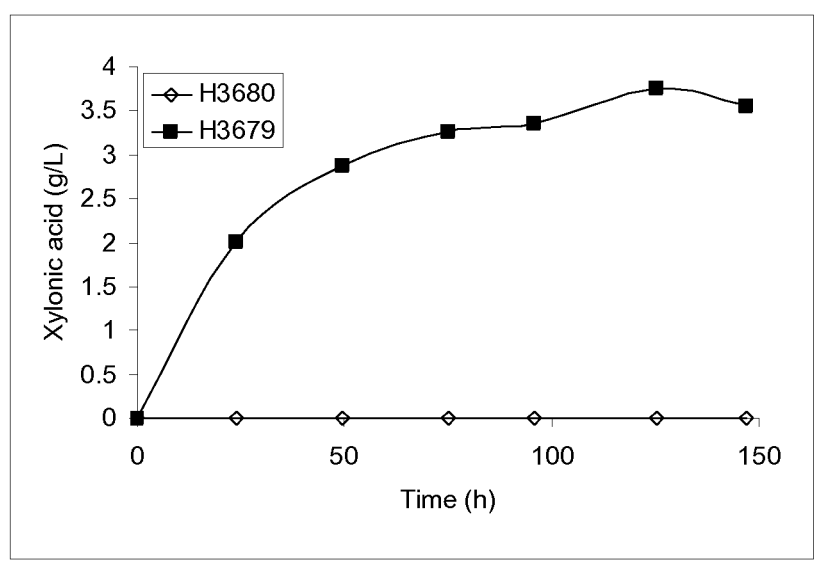
FIG. 14 shows the production of xylonic acid by an *S. cerevisiae* strain expressing an optimized CC_1225 gene of *C. crescentus* (H3679), and the corresponding control strain H3680.

The resulting strains H3679 and H3680 were cultured on SC-medium lacking uracil for plasmid selection, with 10 g l$^{-1}$ glucose and 20 g l$^{-1}$ xylose as carbon sources. The strains were cultured in 250 ml Erlenmeyer flasks in 50 ml medium with 250 rpm agitation at 30° C. Strain H3679 expressing the gene CC_1225 produced 3.3 g xylonic acid l$^{-1}$ extracellularly in 75 h (FIG. 14). Strain H3680 (control strain) produced no xylonic acid when grown under the same conditions.

When strain H3686 was cultured in bioreactor culture, as described in example 7, it produced 13 g xylonate l$^{-1}$. H3686 was also found to be a good strain for the co-production of xylonate and xylitol, producing 11 g xylitol l$^{-1}$, along with the xylonate.

H3698 and H3700 were grown in bioreactor cultures on 10 g glucose l$^{-1}$ and 20 g xylose l$^{-1}$, as described in example 7. H3698 produced 16 g xylonate l$^{-1}$, while H3700 produced 3 g xylonate

Example 12B

Production of Xylonate Using Alternative Xylose Dehydrogenase Integrated into the Genome Strains were constructed in which the gene (SEQ ID NO. 3) encoding a xylose dehydrogenase was integrated into the genome of S. cerevisiae B670002 as a single copy or as two copies. The expression cassette pPGK-xyDHCC0821-tPGK was isolated as a HindIII-fragment from the plasmid pMLV80 and the sticky ends were modified to blunt ends with T4-polymerase. The fragment was ligated into plasmids pMLV23 and pMLV39 which first were digested with BamHI and the ends modified to blunt ends with T4-polymerase. The pMLV23 and pMLV39 contain the loxP-MEL5-loxP or loxP-kan$^r$-loxP marker cassettes flanked with S. cerevisiae GRE3 sequences for integration into the GRE3 locus in S. cerevisiae genome. The BamHI cloning site is included in one of the GRE3 flanking sequences. The plasmids obtained after ligation of the expression cassette for C. crescentus xylose dehydrogenase into pMLV23 and pMLV39 were named pMLV81A or pMLV81B and pMLV82A or pMLV82C, respectively. The labels A, B and C stand for the different orientations of the ligated expression cassette in comparison to the marker cassettes.

The expression cassette for xylose dehydrogenase together with the loxP-kan$^r$-loxP marker was released from the pMLV82C with NotI. The digested DNA was precipitated and transformed into intact B67002 cells treated with LiAc and the kan$^r$-positive yeast colonies were collected from the YPD plates supplemented with G418 (200 μg/ml). For releasing the marker cassette pTEF-kan$^r$-tTEF from the yeast chromosome a purified G418-resistant yeast colony was retransformed with a plasmid pKINatCre expressing the Cre site-specific recombinase and yeast colonies were collected from YPD plates supplemented with antibiotic nourseothricin (50 μg/ml). The Cre recombinase activity in yeast cells was induced by incubating transformants for 3 hours in YP medium supplemented with 2% galactose. The yeast cells that had lost the marker cassette were not able to grow in the presence of G418. The transformants were cured from the plasmid pKINatCre by growing for 20-24 hours in shake flasks in YPD without antibiotic selection. The integration of the expression cassette pPGK-xyDHCC0821-tPGK into GRE3 locus was verified with PCR using sequence specific primers.

For integrating a second copy of the xylose dehydrogenase gene (CC0821) into yeast chromosome the expression cassette together with the loxP-MEL5-loxP marker was released from the pMLV81A (orB) with NatI. The digested DNA was precipitated and transformed into intact B67002/pMLV82C transformant cells treated with LiAc and the MEL5-positive blue coloured yeast colonies were collected from the YP 2% galactose plates supplemented with G418 (200 μg/ml). Both marker cassettes were released simultaneously from the chromosomes by using the Cre-mediated site specific recombination at loxP sites as described above. The yeast cells that had lost both marker cassettes were white in colour and were not able to grow in the presence of G418.

The resulting strains expressing the gene (SEQ ID NO. 3) encoding a xylose dehydrogenase as a single copy or as two copies were grown in flasks and produced 8 to 12 g xylonate l$^{-1}$ in 2 days (approximately 0.17 to 0.25 g l$^{-1}$ h$^{-1}$) when grown in yeast extract-peptone medium with 10 g glucose l$^{-1}$ and 20 g xylose Xylose was completely converted to xylonate in 3 to 4 days. In a bioreactor culture at pH 5.7, up to 50 g xylonate l$^{-1}$ were produced in 4 days in a yeast extract-peptone medium with 15 g glucose l$^{-1}$ and 50 g xylose l$^{-1}$.

Example 13

Production of Xylonate from Hydrolysed Biomass

A fungal strain containing XYD1 can be grown in plant biomass hydrolysate, such as that obtained from distillers dried grain with solubles (DDGS), straw or wood using acid, alkali or enzymatic hydrolysis, to obtain xylonate from the xylose in the hydrolysate. The hydrolysate may be supplemented with specific vitamins or with yeast nitrogen base (YNB, Difco) and may be buffered with $CaCO_3$. The hydrolysate may contain glucose, galactose, xylose and arabinose, and may also contain formate, furfural, 5-(hydroxy-methyl)-2-furaldehyde and other growth inhibitors. It is not necessary to remove precipitated lignin from the hydrolysate suspension prior to addition of the fungus.

TABLE 1

Production characteristics for genetically modified fungi producing xylonic acid and by-products

|  | H3494 pH 5.5 (example 6A) | H3494 pH 3.5 (example 6B) | PR77 pH 5.5 + EtOH (example 7) |
|---|---|---|---|
| Xylonate (g l$^{-1}$) at ~50 h | 1.6 | 1.5 | 1.7 |
| Xylonate (g l$^{-1}$) at ~144 h | 2.7 | 1.6 | 6.1 |
| Specific xylonate (g xylonate [g biomass]$^{-1}$) at ~50 (144) h | 0.52 (0.83) | 0.42 (0.48) | 0.76 (1.80) |
| Xylonate production rate (g xylonate l$^{-1}$ h$^{-1}$) | 0.033 | 0.032 | 0.052 |
| Specific xylonate production rate (g xylonate [g biomass]$^{-1}$ h$^{-1}$) | 0.010 | 0.007 | 0.012 |
| Yield (g xylonate [g xylose]$^{-1}$) | 0.47 | 0.46 | 0.57 |
| Biomass (g l$^{-1}$) at ~50 (144) h | 3.1 ± 0.1 | 3.6 ± 0.1 | 3.1 ± 0.1 (4.2 ± 0.1) |
| Xylitol (g l$^{-1}$) at ~50 h | 1.8 | 1.9 | 1.6 |
| Xylitol production rate (g xylitol l$^{-1}$ h$^{-1}$) | 0.041 | 0.044 | 0.039 |
| Specific xylitol production rate (g xylitol [g biomass]$^{-1}$ h$^{-1}$) | 0.015 | 0.013 | 0.013 |
| Maximum acetate (g l$^{-1}$) | 0.3 | 0.2 | 0.6 |
| Maximum glycerol (g l$^{-1}$) | 0.2 | 0.2 | 0.3 |

TABLE 2

Production characteristics for genetically modified fungi producing xylonic acid and by-products

|  | H3611 pH 5.5 + EtOH (example 7) | H3622 pH 5.5 + EtOH (example 8) |
| --- | --- | --- |
| Xylonate (g $l^{-1}$) at ~50 h | 1.1 | 0.8 |
| Xylonate (g $l^{-1}$) at ~144 h | 3.4 ± 0.3 | 2.0 ± 0.1 |
| Specific xylonate (g xylonate [g biomass]$^{-1}$) at ~50 (144) h | 0.37 (0.76) | 0.29 (0.62) |
| Xylonate production rate (g xylonate $l^{-1}$ $h^{-1}$) | 0.033 | 0.018 |
| Specific xylonate production rate (g xylonate [g biomass]$^{-1}$ $h^{-1}$) | 0.007 | 0.005 |
| Yield (g xylonate [g xylose]$^{-1}$) | 0.44 | 0.60 |
| Biomass (g $l^{-1}$) at ~50 (144) h | 2.9 ± 0.1 (4.6 ± 0.2) | 3.0 ± 0.2 (4.0 ± 0.3) |
| Xylitol (g $l^{-1}$) at ~50 h | 1.8 | 0.6 |
| Xylitol production rate (g xylitol $l^{-1}$ $h^{-1}$) | 0.044 | 0.016 |
| Specific xylitol production rate (g xylitol [g biomass]$^{-1}$ $h^{-1}$) | 0.009 | 0.003 |
| Maximum acetate (g $l^{-1}$) | 0.4 | 0.7 |
| Maximum glycerol (g $l^{-1}$) | 0.3 | 0.3 |

Example 14

Construction of a Issatchenkia orientalis (Candida Krusei) Able to Produce Xylonic Acid Codon optimized synthetic genes based on SEQ ID NO: 3 and SEQ ID NO: 4 are obtained from Gene Art (Germany). The genes are introduced into *I. orientalis* strain ATCC32196 under the PGK1 promoter of *I. orientalis*. The loPGK1 promoter is amplified from the genomic DNA of *I. orientalis* strain ATCC32196 essentially as described in US 2009/0226989 A1. The flanking regions of the loPDC1 gene are obtained essentially as described in US 2009/0226989 A1. The resulting construct contains the loPDC1 flank (5')-loPGK1 promoter-MEL5 marker gene with the MEL5 terminator-loPGK1 promoter-xylose dehydrogenase-*S. cerevisie* PGK1 terminator-loPDC1 flank (3'). The resulting construct is transformed into *I. orientalis* strain ATCC32196. The transformants are selected for blue colour on X-alpha-gal or by growth on melibiose. Transformants are cultured on a xylose containing medium and the culture medium is analyzed for the production of xylonic acid or xylonic acid and xylitol.

SEQUENCES

| SEQ ID NO: | Sequence |
| --- | --- |
| 1 | nt sequence for *T. reesei* XYD1 gene |
| 2 | nt sequence for *H. marismortui* xylose dehydrogenase gene (638184581) |
| 3 | nt sequence for *C. crescentus* xylB gene (CC_0821) |
| 4 | nt sequence for *C. crescentus* CC_1225 gene |
| 5 | nt sequence for pig liver xylose dehydrogenase (NM_214166) |
| 6 | nt sequence for *C. crescentus* xylC gene (CC_0820) |
| 7 | peptide sequence for the protein encoded by *T. reesei* XYD1 gene |
| 8 | protein sequence encoded by *H. marismortui* xylose dehydrogenase gene (638184581) |
| 9 | protein sequence encoded by *C. crescentus* xylB gene (CC_0821) |
| 10 | protein sequence encoded by *C. crescentus* CC_1225 gene |
| 11 | protein sequence encoded by pig liver xylose dehydrogenase (NM_214166) |
| 12 | protein sequence encoded by *C. crescentus* xylC gene (CC_0820) |
| 13 | nt sequence for PCR primer XYD1-a |
| 14 | nt sequence for PCR primer XYD1-b |
| 15 | nt sequence for PCR primer pyrG-5-F |
| 16 | nt sequence for PCR primer pyrG-5-R |
| 17 | nt sequence for PCR primer pyrG-3-F_n |
| 18 | nt sequence for PCR primer pyrG-3-R_n |
| 19 | nt sequence for PCR primer pyrG-del-F_n |
| 20 | nt sequence for PCR primer pyrG-del-R_n |
| 21 | nt sequence for PCR primer GRE3del-a |
| 22 | nt sequence for PCR primer GRE3del_b |
| 23 | nt sequence for PCR primer xyrA-5-F_n |
| 24 | nt sequence for PCR primer xyrA-5-R_n |
| 25 | nt sequence for PCR primer xyrA-3-F |
| 26 | nt sequence for PCR primer xyrA-3-R |
| 27 | nt sequence for PCR primer GRE3_a |
| 28 | nt sequence for PCR primer GRE3_b |
| 29 | nt sequence for PCR primer xyrA-ORF-F |
| 30 | nt sequence for PCR primer xyrA-ORF-R |
| 31 | nt sequence for primer KIXYL1p_1YE1 |
| 32 | nt sequence for primer KIXYL1p_2KMXp |
| 33 | nt sequence for primer KIXYL1t_KMXt |
| 34 | nt sequence for primer KIXYL1t_YE2 |
| 35 | nt sequence for primer KIXDHp1KMXt |
| 36 | nt sequence for primer KIXDHp2YE2 |
| 37 | nt sequence for primer KIXDHt1YE1 |
| 38 | nt sequence for primer KIXDHt2KMXp |
| 39 | nt sequence for primer recCC00820F |
| 40 | nt sequence for primer recCC00820R |

The invention claimed is:

1. A method for producing xylonic acid, comprising:
providing a fungal host that is genetically modified to express a cytoplasmic xylose dehydrogenase encoding gene;
culturing the host in a xylose-containing medium to obtain xylonic acid;
recovering the xylonic acid directly from the medium without disrupting the cells.

2. The method of claim 1, wherein the xylose-containing medium further comprises an energy source selected from the group consisting of ethanol, glucose, fructose, galactose, L-arabinose, glycerol, and acetate.

3. The method of claim 1, wherein the xylose-containing medium is a hemicellulosehydrolysate.

4. The method of claim 1, wherein xylonic acid is produced together with a sugar alcohol, or with a second sugar acid.

5. The method of claim 1, wherein culturing comprises culturing the host at a pH of from 3.0 to 6.5.

6. The method of claim 1, wherein the fungal host is a genera selected from the group consisting of *Saccharomyces, Kluyveromyces, Candida,* and *Aspergillus*.

7. The method of claim 1, wherein the xylose dehydrogenase encoding gene is isolated from yeast, a filamentous fungus, an Archaean, a plant, a mammal or a bacterium.

8. The method of claim 1, wherein the xylose dehydrogenase gene is isolated from *Trichoderma reesei, Haloarcula marismortui,* or *Caulobacter crescentus*.

9. The method of claim 1, wherein the xylose dehydrogenase gene is Xyd1 of *Trichoderma reesei*.

10. The method of claim 1, wherein the fungal host has been further modified to overexpress an aldose reductase gene, or has been further modified to produce a sugar alcohol or a second sugar acid together with the xylonic acid.

11. The method of claim 1, wherein the fungal host has been further modified to express a lactonase gene.

12. The method of claim 1, further comprising after culturing the host in a xylose-containing medium, removing host cells from the spent culture medium and recovering cell free spent culture medium containing xylonic acid.

13. The method of claim 1, wherein the xylonic acid is isolated and purified from the medium.

14. The method of claim 1, wherein the fungal host cell is further genetically modified by disrupting or deleting one or more aldose or xylose reductase genes.

* * * * *